(12) United States Patent
Enomura et al.

(10) Patent No.: US 10,835,458 B2
(45) Date of Patent: Nov. 17, 2020

(54) SILICON OXIDE-COATED OXIDE COMPOSITION FOR COATING IN WHICH WEATHER RESISTANCE IS REQUIRED, AND METHOD OF PRODUCING COMPOSITION FOR COATING

(71) Applicant: M. TECHNIQUE CO., LTD., Izumi (JP)

(72) Inventors: Masakazu Enomura, Izumi (JP); Daisuke Honda, Izumi (JP)

(73) Assignee: M. TECHNIQUE CO., LTD., Izumi (JP)

( * ) Notice: Subject to any disclaimer, the term of this patent is extended or adjusted under 35 U.S.C. 154(b) by 382 days.

(21) Appl. No.: 15/571,194

(22) PCT Filed: Oct. 5, 2016

(86) PCT No.: PCT/JP2016/079710
§ 371 (c)(1),
(2) Date: Nov. 1, 2017

(87) PCT Pub. No.: WO2017/061520
PCT Pub. Date: Apr. 13, 2017

(65) Prior Publication Data
US 2019/0153246 A1    May 23, 2019

(30) Foreign Application Priority Data

Oct. 5, 2015 (JP) .................................. 2015-197556
Jun. 2, 2016 (JP) .................................. 2016-111346
(Continued)

(51) Int. Cl.
*C09D 7/61* (2018.01)
*C09D 7/40* (2018.01)
(Continued)

(52) U.S. Cl.
CPC .............. *A61K 8/0245* (2013.01); *A61K 8/04* (2013.01); *A61K 8/19* (2013.01); *A61K 8/25* (2013.01);
(Continued)

(58) Field of Classification Search
None
See application file for complete search history.

(56) References Cited

U.S. PATENT DOCUMENTS

| 4,487,869 A | 12/1984 | Panush |
| 5,340,393 A | 8/1994 | Jacobson |

(Continued)

FOREIGN PATENT DOCUMENTS

| EP | 0 595 471 A2 | 5/1994 |
| EP | 0 988 853 A1 | 3/2000 |

(Continued)

OTHER PUBLICATIONS

International Search Report, issued in PCT/JP2016/066542, dated Aug. 2, 2016.
(Continued)

*Primary Examiner* — Alexandre F Ferre
(74) *Attorney, Agent, or Firm* — Birch, Stewart, Kolaasch & Birch, LLP

(57) ABSTRACT

A silicon oxide-coated oxide composition for coating is disclosed in which color characteristics, particularly reflectivity are controlled, and a method of producing a composition for coating is disclosed which is used by blending the composition for coating to a paint constituting a coated body in which weather resistance is required. The silicon oxide-coated oxide composition for coating in which weather resistance is required includes silicon oxide-coated oxide particles wherein at least a part of the surface of the oxide particles is coated with silicon oxide, wherein the silicon
(Continued)

oxide is amorphous for the purpose of controlling color characteristics of the silicon oxide-coated oxide composition for coating. The method of producing the composition for coating, wherein color characteristics of the oxide particles are controlled, includes producing the oxide particles by selecting presence or absence of amorphous silicon oxide covering at least a part of the surface of the oxide particles, and presence or absence of an acetyl group as a functional group contained in the silicon oxide-coated oxide particles.

8 Claims, 13 Drawing Sheets

(30) Foreign Application Priority Data

Jun. 3, 2016 (WO) .................. PCT/JP2016/066542
Jun. 22, 2016 (JP) ................................ 2016-123800

(51) Int. Cl.

| | |
|---|---|
| *C09C 3/06* | (2006.01) |
| *C09D 5/33* | (2006.01) |
| *C09D 1/00* | (2006.01) |
| *C01B 33/12* | (2006.01) |
| *C01G 9/02* | (2006.01) |
| *A61K 8/02* | (2006.01) |
| *C09C 1/04* | (2006.01) |
| *C09C 1/24* | (2006.01) |
| *C09C 3/08* | (2006.01) |
| *A61K 8/04* | (2006.01) |
| *A61K 8/19* | (2006.01) |
| *A61K 8/25* | (2006.01) |
| *A61K 8/49* | (2006.01) |
| *A61Q 1/02* | (2006.01) |
| *A61Q 17/04* | (2006.01) |
| *C09D 5/32* | (2006.01) |
| *C01B 13/36* | (2006.01) |
| *C08K 3/34* | (2006.01) |
| *C08K 3/22* | (2006.01) |
| *C08K 9/02* | (2006.01) |
| *B82Y 30/00* | (2011.01) |

(52) U.S. Cl.

CPC .............. *A61K 8/4926* (2013.01); *A61Q 1/02* (2013.01); *A61Q 17/04* (2013.01); *C01B 13/36* (2013.01); *C01B 33/12* (2013.01); *C01G 9/02* (2013.01); *C08K 3/34* (2013.01); *C09C 1/043* (2013.01); *C09C 1/24* (2013.01); *C09C 3/063* (2013.01); *C09C 3/08* (2013.01); *C09D 1/00* (2013.01); *C09D 5/004* (2013.01); *C09D 5/32* (2013.01); *C09D 7/61* (2018.01); *C09D 7/67* (2018.01); *A61K 2800/413* (2013.01); *A61K 2800/43* (2013.01); *A61K 2800/621* (2013.01); *A61K 2800/651* (2013.01); *B82Y 30/00* (2013.01); *C01P 2002/72* (2013.01); *C01P 2002/82* (2013.01); *C01P 2004/04* (2013.01); *C01P 2004/32* (2013.01); *C01P 2004/64* (2013.01); *C01P 2004/84* (2013.01); *C08K 9/02* (2013.01); *C08K 2003/2265* (2013.01); *C08K 2201/003* (2013.01); *C08K 2201/011* (2013.01)

(56) References Cited

U.S. PATENT DOCUMENTS

| | | |
|---|---|---|
| 5,827,507 A | 10/1998 | Oshima et al. |
| 5,914,101 A | 6/1999 | Tapley et al. |
| 2002/0037262 A1 | 3/2002 | Tanaka et al. |
| 2009/0017082 A1 | 1/2009 | Morimitsu et al. |
| 2010/0008872 A1* | 1/2010 | Katusic .................... A61K 8/25 424/59 |
| 2010/0040567 A1 | 2/2010 | Katusic et al. |
| 2010/0155310 A1 | 6/2010 | Enomura |
| 2012/0130023 A1* | 5/2012 | Herzog .................. B82Y 30/00 525/386 |
| 2014/0037519 A1 | 2/2014 | Kuraki et al. |
| 2015/0030760 A1 | 1/2015 | Enomura |
| 2015/0202655 A1 | 7/2015 | Nakano et al. |
| 2015/0217332 A1 | 8/2015 | Fujii et al. |

FOREIGN PATENT DOCUMENTS

| | | |
|---|---|---|
| GB | 2518202 A | 3/2015 |
| JP | 59-75960 A | 4/1984 |
| JP | 60-106866 A | 6/1985 |
| JP | 63-54979 A | 3/1988 |
| JP | 6-192593 A | 7/1994 |
| JP | 7-506081 A | 7/1995 |
| JP | 8-12961 A | 1/1996 |
| JP | 10-130021 A | 5/1998 |
| JP | 2000-2274 A | 1/2000 |
| JP | 2001-270225 A | 10/2001 |
| JP | 2003-277644 A | 10/2003 |
| JP | 2008-239460 A | 10/2008 |
| JP | 2009-67613 A | 4/2009 |
| JP | 2009-112892 A | 5/2009 |
| JP | 2009-263547 A | 11/2009 |
| JP | 2009-545509 A | 12/2009 |
| JP | 2010-508229 A | 3/2010 |
| JP | 4868558 B1 | 2/2012 |
| JP | 2014-42891 A | 3/2014 |
| JP | 2014-42892 A | 3/2014 |
| WO | WO 98/26011 A1 | 6/1998 |
| WO | WO 98/47476 A1 | 10/1998 |
| WO | WO 2009/008393 A1 | 1/2009 |
| WO | WO 2013/128592 A1 | 9/2013 |

OTHER PUBLICATIONS

International Search Report, issued in PCT/JP2016/079710, dated Nov. 29, 2016.
Extended European Search Report for corresponding European Application No. 16853674.6, dated May 14, 2019.
Peng et al., "Multifunctional silica-coated iron oxide nanoparticles: a facile four-in-one system for in situ study of neural stem cell harvesting," Faraday Discussions, vol. 175, Jul. 28, 2014, pp. 13-26 (15 pages total).

* cited by examiner

SILICON OXIDE-COATED OXIDE COMPOSITION FOR COATING IN WHICH WEATHER RESISTANCE IS REQUIRED, AND METHOD OF PRODUCING COMPOSITION FOR COATING

TECHNICAL FIELD

The present invention relates to a silicon oxide-coated oxide composition for coating in which weather resistance is required, and a method of producing a composition for coating.

BACKGROUND ART

Oxide particles are materials used in a wide range of fields such as catalysts, conductive materials, magnetic materials, secondary electron emission materials, luminous bodies, heat absorbers, energy storage bodies, electrode materials, colorants, and the like. Since characteristics are changeable depending on particle size of the particles, oxide particles having different particle size and crystallinity are required depending on the purpose or requirements. In particular, significantly different characteristics from those in a bulk state are exhibited by micronization of oxide particles, and thus, oxide particles are widely sought materials now and in future. However, when two or more characteristics exhibited by micronization exist, there are cases that exhibition of only specific charateristics and suppression of other characteristics are desired depending on their usage. As an example, while both photocatalytic ability and ultraviolet absorbing ability are exhibited by micronization of metal oxide, suppression of photocatalyst is needed in case of using metal oxides microparticles as a colorant or ultraviolet protective agent.

A paint material for the purpose of coating is one of their usages. Weather resistance is required for a paint used to exterior walls and signboards in building materials, and vehicles and the like, because the objects are light resistance against degradation by sunlight irradiation, and durability against environmental change associated with weather changes, and protection of a paint and a coated body from the degradation of components and the like included in the coated body by salt damage or the above mentioned photocatalytic activity.

In Patent Literature 1, oxide powders are dispersed in water containing an organic solvent, and the surface of the oxide particles are coated with silica for suppressing the photocatalytic activity by treatment with a silicon compound. Patent Literature 2 discloses as an iron oxide for protection from ultraviolet rays or near infrared rays, a coloring pigment for sunlight high reflecting coating, comprising red iron oxide or yellow hydrous iron oxide having an average particle diameter of 10 to 300 nm. Patent Literature 3 discloses an iron oxide as a needle-shaped silica-coated Bengara red pigment having an average length of 500 nm and an average diameter of 100 nm. The iron oxide described in Patent Literatures 1 to 3 may be used by mixing with the paint described in Patent Literature 6 or 7.

In the case of using the oxide particles in a paint and a coated body, the color characteristics of the oxide particles themselves are as important as those of the coloring material contained in the paint and the coated body. However, Patent Literatures 1 to 3 describes the silica coating for inhibition of photocatalytic activity in the described silica-coated iron oxide, but does not describe specific silica coating for controlling color characteristics.

Patent Literature 4 filed by the present applicant discloses a method of producing particles between two processing surfaces being capable of approaching to and separating from each other and rotating relative to each other. However, the method described in Patent Literature 4 is a method of producing oxide particles efficiently and stably, but a method of producing oxide particles which surface is coated with silicon oxide is not disclosed. Further, Patent Literature 5 discloses a method of producing a method of producing various nanoparticles of an iron oxide and the like between two processing surfaces being capable of approaching to and separating from each other and rotating relative to each other. However, the iron oxide nanoparticles described in Patent Literature 5 are the nanoparticles of black iron oxide ($Fe_3O_4$: magnetite) and yellow iron oxide (FeOOH: goethite), and it is not described that specific color characteristics exhibited by these iron oxide nanoparticles are controlled. In the first place, Patent Literature 4 and Patent Literature 5 do not show even suppression of specific color characteristics exhibited by these iron oxide nanoparticles. Color characteristics exhibited by oxide particles themselves have not sufficiently studied so far.

CITATION LIST

Patent Literature

Patent Literature 1: WO 98/47476
Patent Literature 2: JP 2009-263547
Patent Literature 3: WO 98/26011
Patent Literature 4: JP 4868558
Patent Literature 5: WO 2009/008393
Patent Literature 6: JP 2014-042891
Patent Literature 7: JP 2014-042892

SUMMARY OF THE INVENTION

Technical Problem

In light of such circumstances, an object of the present invention is to provide a silicon oxide-coated oxide composition for coating which color characteristics are controlled. Especially, an object of the present invention is to provide a silicon oxide-coated oxide composition for coating which reflectivity is particularly controlled.

Furthermore, an object of the present invention is to provide a composition for coating which is used by blending the composition for coating to a paint constituting a coated body in which weather resistance is required, which is a silicon oxide-coated oxide composition for coating, and may be effectively used for a coated body having various colors.

Furthermore, an object of the present invention is to provide a method of producing a composition for coating comprising oxide particles, which is used by blending the composition for coating to a paint constituting a coated body in which weather resistance is required, wherein color characteristics of the oxide particles are effectively controlled.

Solution to the Problem

The present invention provides a silicon oxide-coated oxide composition for coating in which weather resistance is required, which comprises silicon oxide-coated oxide particles wherein at least a part of the surface of the oxide particles is coated with silicon oxide, wherein the silicon oxide is amorphous for the purpose of controlling color characteristics of the silicon oxide-coated oxide composition for coating.

Here, all silicon oxide is not needed to be amorphous, but may include amorphous silicon oxide, as long as color characteristics of the silicon oxide-coated oxide composition for coating can be controlled. The term "silicon oxide is amorphous" in the present invention means, unless otherwise specified, that silicon oxide includes amorphous silicon oxide.

In the present invention, the color characteristics are preferably reflectivity.

In the present invention, a particle diameter of the silicon oxide-coated oxide particles is preferably 1 to 50 nm.

In the present invention, color characteristics of the silicon oxide-coated oxide composition for coating can be controlled by changing a functional group included in the silicon oxide-coated oxide particles.

Further, the present invention provides a composition for coating, which is used by blending the composition for coating to a paint constituting a coated body in which weather resistance is required, wherein the composition for coating comprises silicon oxide-coated oxide particles which comprise oxide particles and silicon oxide wherein at least a part of the surface of the oxide particles is coated with the silicon oxide, wherein the silicon oxide is amorphous, and wherein the silicon oxide-coated oxide particles are constituted so that reflectivity for the light of 380 to 780 nm is higher than that of oxide particles which surface is not coated with silicon oxide.

Further, the present invention provides a composition for coating, which is used by blending the composition for coating to a paint constituting a coated body in which weather resistance is required, wherein the composition for coating comprises silicon oxide-coated oxide particles which comprise oxide particles and silicon oxide wherein at least a part of the surface of the oxide particles is coated with the silicon oxide, wherein the silicon oxide-coated oxide particles comprise an acetyl group as a functional group, and wherein the silicon oxide-coated oxide particles are constituted so that reflectivity for the light of 550 to 800 nm is lower than that of oxide particles which surface is not coated with silicon oxide.

In the present invention, the silicon oxide-coated oxide particles are preferably silicon oxide-coated iron oxide particles or silicon oxide-coated zinc oxide particles.

Further, the present invention provides a method of producing a composition for coating comprising oxide particles, which is used by blending the composition for coating to a paint constituting a coated body in which weather resistance is required, wherein color characteristics of the oxide particles are controlled by producing the oxide particles by selecting presence or absence of amorphous silicon oxide covering at least a part of the surface of the oxide particles, and presence or absence of an acetyl group as a functional group contained in the silicon oxide-coated oxide particles.

Further, the present invention provides a composition for coating, which is used by blending the composition for coating to a paint constituting a coated body in which weather resistance is required, wherein the composition for coating comprises silicon oxide-coated oxide particles which comprise oxide particles and silicon oxide wherein at least a part of the surface of the oxide particles is coated with the silicon oxide, wherein the oxide particles are zinc oxide particles, wherein the silicon oxide-coated oxide particles are those wherein at least a part of the surface of one oxide particle is coated with silicon oxide, wherein a particle diameter of the oxide particle is 100 nm or less, and the primary particle diameter of the silicon oxide-coated oxide particles is 100.5% or more and 190% or less relative to the primary particle diameter of the oxide particle, and wherein the silicon oxide-coated oxide particles are constituted so that reflectivity for the light of 380 to 780 nm is higher than that of oxide particles which surface is not coated with silicon oxide.

Further, the present invention provides a composition for coating, which is used by blending the composition for coating to a paint constituting a coated body in which weather resistance is required, wherein the composition for coating comprises silicon oxide-coated oxide particles which comprise oxide particles and silicon oxide wherein at least a part of the surface of the oxide particles is coated with the silicon oxide, wherein the oxide particles are zinc oxide particles, wherein the silicon oxide-coated oxide particles are those wherein at least a part of the surface of an aggregate of a plurality of oxide particles is coated with silicon oxide, wherein a diameter of the aggregate is 100 nm or less, and the particle diameter of the silicon oxide-coated oxide particles is 100.5% or more and 190% or less relative to the diameter of the aggregate, and wherein the silicon oxide-coated oxide particles are constituted so that reflectivity for the light of 380 to 780 nm is higher than that of oxide particles which surface is not coated with silicon oxide.

Further, the present invention provides a composition for coating, which is used by blending the composition for coating to a paint constituting a coated body in which weather resistance is required, wherein the composition for coating comprises silicon oxide-coated oxide particles which comprise oxide particles and silicon oxide wherein at least a part of the surface of the oxide particles is coated with the silicon oxide, wherein the oxide particles are iron oxide particles, wherein the silicon oxide-coated oxide particles are those wherein at least a part of the surface of one oxide particle is coated with silicon oxide, wherein a particle diameter of the oxide particle is 50 nm or less, and the primary particle diameter of the silicon oxide-coated oxide particles is 100.5% or more and 190% or less relative to the primary particle diameter of the oxide particle, and wherein the silicon oxide-coated oxide particles are constituted so that reflectivity for the light of 550 to 800 nm is lower than that of oxide particles which surface is not coated with silicon oxide.

Further, the present invention provides a composition for coating, which is used by blending the composition for coating to a paint constituting a coated body in which weather resistance is required, wherein the composition for coating comprises silicon oxide-coated oxide particles which comprise oxide particles and silicon oxide wherein at least a part of the surface of the oxide particles is coated with the silicon oxide, wherein the oxide particles are iron oxide particles, wherein the silicon oxide-coated oxide particles are those wherein at least a part of the surface of an aggregate of a plurality of oxide particles is coated with silicon oxide, wherein a diameter of the aggregate is 50 nm or less, and the particle diameter of the silicon oxide-coated oxide particles is 100.5% or more and 190% or less relative to the diameter of the aggregate, and wherein the silicon oxide-coated oxide particles are constituted so that reflectivity for the light of 550 to 800 nm is lower than that of oxide particles which surface is not coated with silicon oxide.

Further, in the present invention, the silicon oxide-coated oxide particles can comprise an acetyl group as a functional group.

Further, the present invention, the silicon oxide can comprise amorphous silicon oxide.

Advantageous Effects of the Invention

The present invention can provide a silicon oxide-coated oxide composition for coating which color characteristics are controlled. The present invention can provide a silicon oxide-coated oxide composition for coating which reflectivity is particularly controlled, and thus, the present invention can provide a composition for coating protecting a coated body in which weather resistance is required, which is used by blending the composition for coating to a paint constituting a coated body, which is a silicon oxide-coated oxide composition for coating, and may be effectively used for a coated body having various colors. Furthermore, the present invention can provide a method of producing a composition for coating comprising oxide particles, which is used by blending the composition for coating to a paint constituting a coated body in which weather resistance is required, wherein color characteristics of the oxide particles are effectively controlled.

DESCRIPTION OF THE INVENTION

Figure 1:
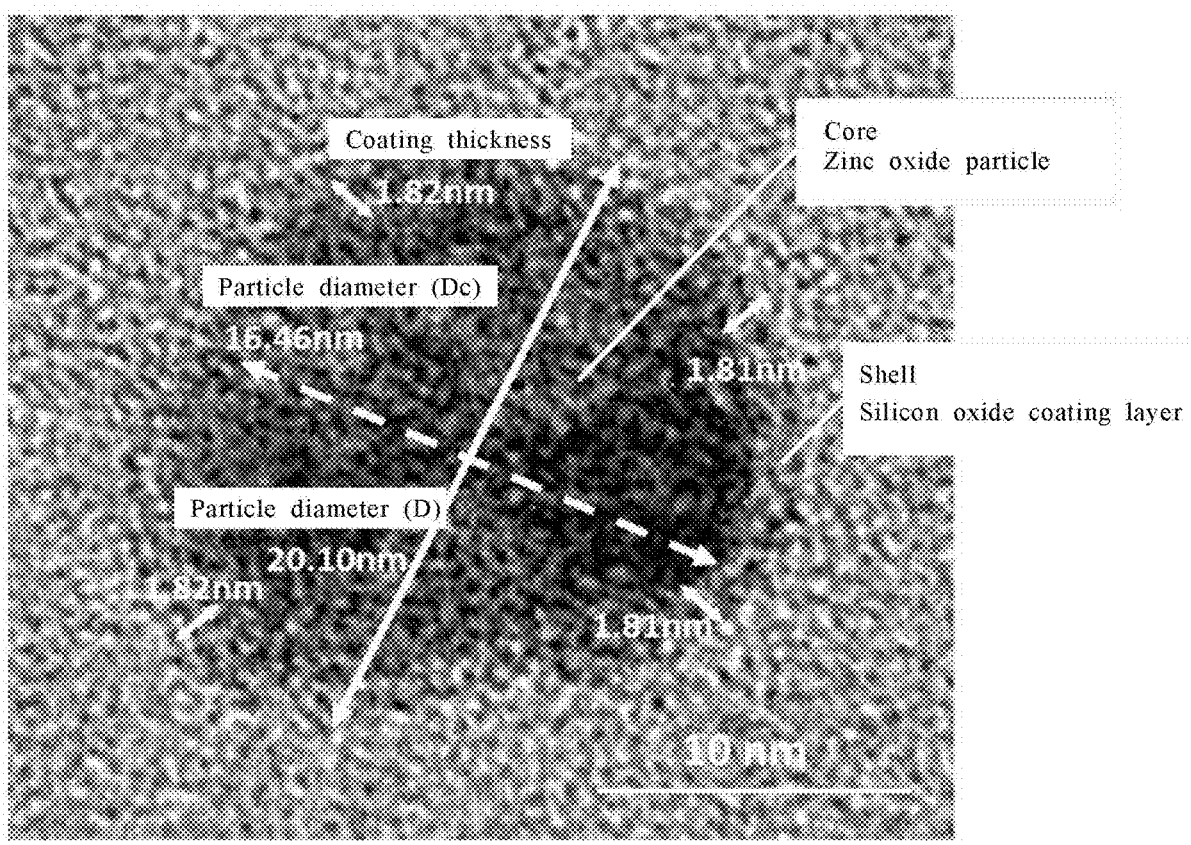
FIG. 1 shows a TEM photograph of the silicon oxide-coated zinc oxide particles obtained in Example 1 of the present invention.

Hereinafter, the present invention is explained by embodiments of the present invention based on the drawings as an example. However, embodiments of the present invention are not limited only to the embodiments described hereinafter.

Silicon oxide-coated oxide particles of the present invention refer to oxide particles in which at least a part of the surface of the oxide particles is coated with amorphous silicon oxide, and may be core-shell type silicon oxide-coated oxide particles wherein the entire surface of a core oxide particle is uniformly coated with silicon oxide. Further, the silicon oxide-coated oxide particles are not limited as long as they have specific controlled color characteristics, but preferred are silicon oxide-coated oxide particles wherein a plurality of oxide particles are not aggregated, and at least a part of the surface of one oxide particle is coated with silicon oxide. Also preferred are silicon oxide-coated oxide particles wherein at least a part of the surface of an aggregate of a plurality of oxide particles is coated with silicon oxide.

Further, it is preferable that the oxide particles are zinc oxide particles or iron oxide particles, because a variety of usage is possible in using as a composition for coating. When oxide particles are zinc oxide particles, it is possible to use them particularly as a composition for coating intended for a clear coating film or a white pigment, and to use them suitably as a composition for coating by mixing them with another pigment or the like. When oxide particles are iron oxide particles, it is possible to use them particularly as a composition for coating intended for a clear coating film for a red color painting or a red pigment, and to use them suitably as a composition for coating by mixing them with another pigment or the like. Thus, silicon oxide coating at least part of the surface of oxide particles preferably comprises amorphous silicon oxide.

The oxide particles should be interpreted to mean the particles composed of oxide as a main component. Even when particles include impurities mixed unintentionally or other components added intentionally, such particles are included in the oxide particles in the present invention as long as the oxide is included in the particles more than other components in terms of a part by weight or a molar ratio.

In addition, for example, at least a part of the surface of oxide particles such as titanium oxide, lead oxide, cobalt oxide, chromium oxide and the like, or composite oxide particles comprising a plurality of elements other than oxygen, and the like can be coated with silicon oxide. Color characteristics exhibited by the respective oxide particles can be controlled by coating with the amorphous silicon oxide. Though the details are not clear, a silicon oxide-coated oxide particles of the present invention has (1) oxygen from the oxide particles, (2) a specific metal such as zinc and iron from the oxide particles, (3) oxygen on the surface of the oxide particles, (4) silicon from the silicon oxide coating the surface of the oxide particles, (5) oxygen from the silicon oxide coating the surface of the oxide particles. It is possible that a bond is formed between each element above, for example, the bonds: (1)-(2)-(3)-(4)-(5). Such bond may affect crystallinity of the surface of the oxide particles, or strain in the bond may occur, because silicon oxide coating at least a part of the surface of the oxide is amorphous. Thus, color characteristics exhibited by oxide particles can be controlled. The inventors consider the above mechanism may be another possibility for control of color characteristics of a silicon oxide-coated oxide composition for coating of the present invention. Not particularly limited, the inventors consider that it is another possible factor for control of color characteristics of a silicon oxide-coated oxide composition for coating of the present invention, that the oxide particles are crystalline, and silicon oxide coating at least a part of the surface of the oxide particles is amorphous.

Further in the present invention, color characteristics of the silicon oxide-coated oxide composition for coating may be controlled by changing a functional group contained in the silicon oxide-coated oxide particles. Though the details are not clear, the inventors consider that color characteristics of the silicon oxide-coated oxide composition for coating can be controlled by controlling an element and a functional group bonding to the oxygen in above (3) or (5). For example, when hydrogen bonds to the oxygen in (3) or (5), hydroxyl groups are present on the surface of the silicon oxide-coated oxide particles. The hydroxyl group may be replaced by another functional group such as an acyl group and benzoyl group. Different types of functional groups have properties of absorption and vibration against a light of a specific wavelength respectively. The properties of absorption and vibration against a light on the surface of a silicon oxide-coated oxide particles can be changed by changing a functional group contained in the silicon oxide-coated oxide particles of the present invention, including a functional group bonding to the oxygen of above (3) or (5). Therefore, the present inventors consider that color characteristics of the silicon oxide-coated oxide composition for coating can be controlled by changing a functional group contained in a silicon oxide-coated oxide particles of the present invention. Since influence of the fluorescence emission was considered, the fluorescence spectra were measured for silicon oxide-coated oxide particles before and after changing the functional group contained in the silicon oxide-coated oxide particles, using the fluorescence spectrophotometer (product name: FP-6500, JASCO Corporation), with excitation wavelength of 220 to 750 nm, in the measuring range of the fluorescence wavelength of 220 to 750 nm. No fluorescence was observed in both spectra.

Furthermore, since the particle diameter of the oxide particles constituting silicon oxide-coated oxide particles of the present invention as well as the particle diameter of the silicon oxide-coated oxide particles are minute, and a coating rate of the silicon oxide to the total silicon oxide-coated oxide particles is increased. Thus, the inventors consider that it would be also a possible factor for control of the color characteristics, that the above bonds: oxygen-specific metal-oxygen-silicon-oxygen (functional group) are increased.

In the present invention, the diameter of the oxide particles constituting the above silicon oxide-coated oxide particles is preferably 1 to 100 nm, and is more preferably 1 to 50 nm. Further, it is preferable that the particle diameter of the silicon oxide-coated oxide particles is 100.5% or more and 190% or less relative to the particle diameter of the above oxide particles. Silicon oxide-coated oxide particles of the present invention may be silicon oxide-coated oxide particles wherein at least a part of the surface of the aggregate of a plurality of the oxide particles is coated with silicon oxide. However, a silicon oxide-coated oxide wherein an aggregate exceeding a certain size are coated with silicon oxide is not preferable, since such silicon oxide-coated oxide particles may not have the effect of color characteristics such as reflectivity and the like, compared with silicon oxide-coated oxide particles wherein at least a part of the surface of one iron oxide particle is coated with silicon oxide. The particle diameter of the silicon oxide-coated oxide particles is preferably not more than 190% of the particle diameter of the oxide particles. Here, the aggregate exceeding a certain size refers to those which diameter is, for example, more than 100 nm in case of an aggregate of zinc oxide, and more than 50 nm in case of an aggregate of iron oxide. When silicon oxide coating is too thin relative to the oxide particles, the effect regarding the color characteristics of the silicon oxide-coated oxide particles may not exhibit. Thus, it is preferable that the particle diameter of the silicon oxide-coated oxide particles is not less than 100.5% relative to the particle diameter of the oxide particles. When the coating is too thick, or when a coarse aggregate is coated, control of color characteristics is difficult. Thus, it is preferable that the particle diameter of the silicon oxide-coated oxide particles is not more than 190% relative to the particle diameter of the oxide particles. Here, a diameter of the aggregate refers to a maximum distance between two points on the outer periphery of the aggregate.

A silicon oxide-coated oxide composition for coating in which weather resistance is required of the present invention, comprises powers of silicon oxide-coated oxide particles; a dispersion wherein silicon oxide-coated oxide particles are dispersed in a liquid dispersion medium; and a dispersion wherein silicon oxide-coated oxide particles are dispersed in a solid such as glass and resin, and the like. Silicon oxide-coated oxide particles included in the silicon oxide-coated oxide composition for coating may be composed of silicon oxide-coated oxide particles wherein at least a part of the surface of one oxide particle is coated with silicon oxide, or may be composed of silicon oxide-coated oxide particles wherein at least a part of the surface of the aggregate of a plurality of oxide particles is coated with silicon oxide, or may be composed of both of those. Further, the silicon oxide-coated oxide composition for coating may be used dispersed in a paint together with various pigments, or may be overcoated on a coating film. Further, the silicon oxide-coated oxide composition of the present invention may be used as a sole pigment. A liquid dispersion medium includes water such as tap water, distilled water, RO water, pure water and ultrapure water; an alcohol solvent such as methanol, ethanol and isopropyl alcohol; a polyhydric alcohol solvent such as propylene glycol, ethylene glycol, diethylene glycol and glycerine; an ester solvent such as ethyl acetate and butyl acetate; an aromatic solvent such as benzene, toluene and xylene; a ketone solvent such as acetone and methyl ethyl ketone; a nitrile solvent such as acetonitrile, and the like. These dispersion media may be used alone or may be used by mixing a plurality of these dispersion media.

Weather resistance is required for a silicon oxide-coated oxide composition for coating of the present invention, because the objects are light resistance against degradation by sunlight irradiation, and treatment against environmental change associated with weather or humidity changes and the like, and protection of a paint and a coated body from the degradation of components and the like included in the coated body by salt damage or photocatalytic activity. However, in order to achieve the above object, in case of using a conventional silicon oxide-coated oxide for coating, color characteristics such as a tint generated from the coated body, its chroma, transparency, and designability of a product may be impaired, and desired color characteristics may not be obtained.

In the present invention, color characteristics, particularly reflectivity, of a silicon oxide-coated oxide composition can be controlled by making silicon oxide in the silicon oxide-coated oxide particles be amorphous as explained later.

Figure 2:
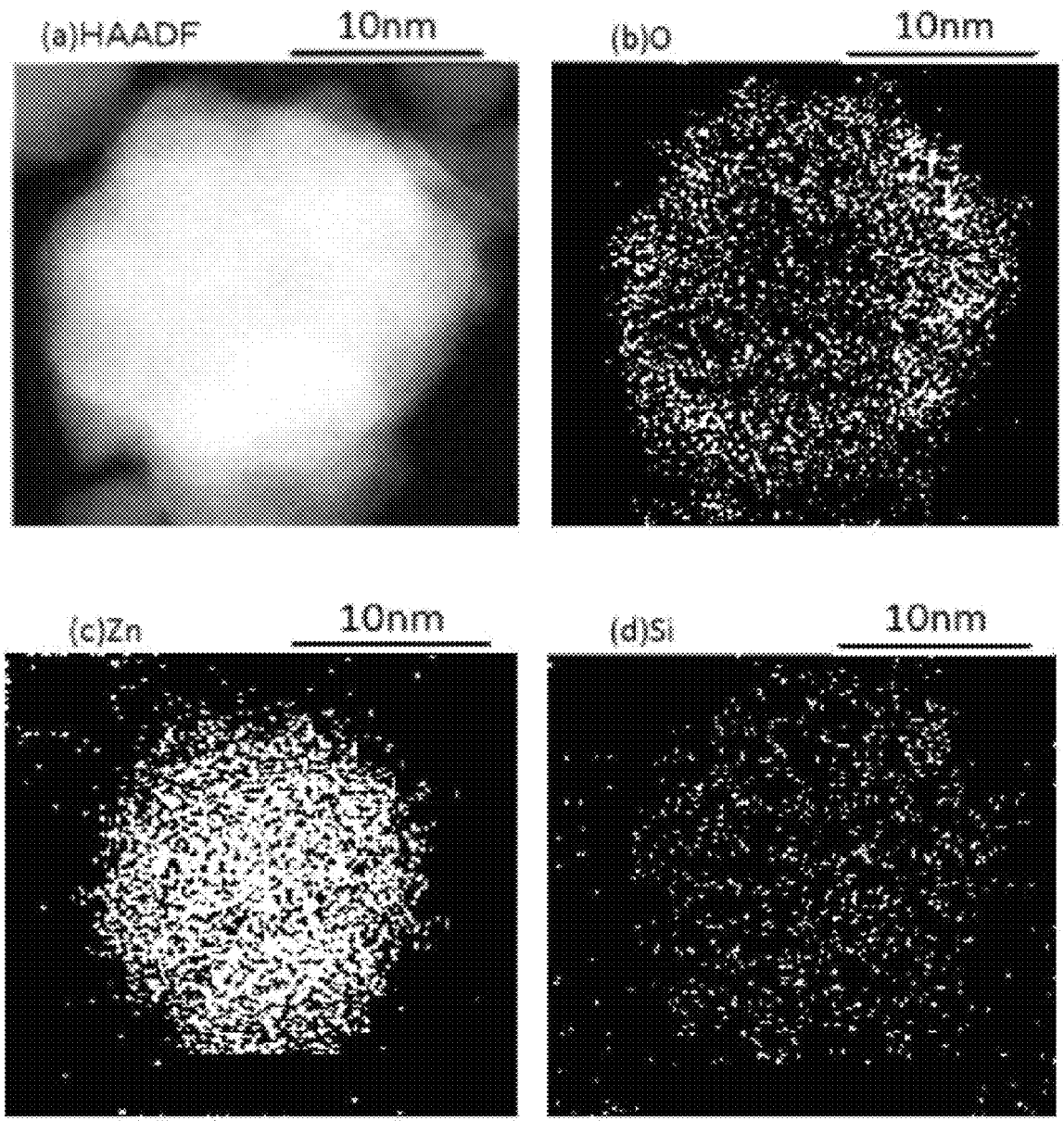
FIG. 2 shows an STEM mapping of the silicon oxide-coated zinc oxide particles obtained in Example 1 of the present invention.

FIG. 1 shows a TEM photograph of the zinc oxide particles coated with silicon oxide (hereinafter, referred to as silicon oxide-coated zinc oxide particles) obtained in Example 1 as described below. FIG. 2 shows a STEM mapping result of the particles. As shown in FIG. 1, core-shell type silicon oxide-coated zinc oxide particles wherein the entire surface of one zinc oxide particle as a core is uniformly coated with silicon oxide, are observed, and a coating layer (shell layer) of silicon oxide having a thickness of about 1.8 nm on the entire surface of the core zinc oxide particle is observed. In the STEM mapping result shown in FIG. 2, (a) shows a mapping of a dark-field image (HADDF image), (b) shows a mapping of oxygen (O), (c) shows a mapping of zinc (Zn), and (d) shows a mapping of silicon (Si). Regarding the particles observed in the HADDF image, distribution of oxygens (O) and silicons (Si) was observed in the entire particles, and distribution of zinc (Zn) was observed in about 1.8 nm smaller area in radius compared with the particles.

Figure 3:
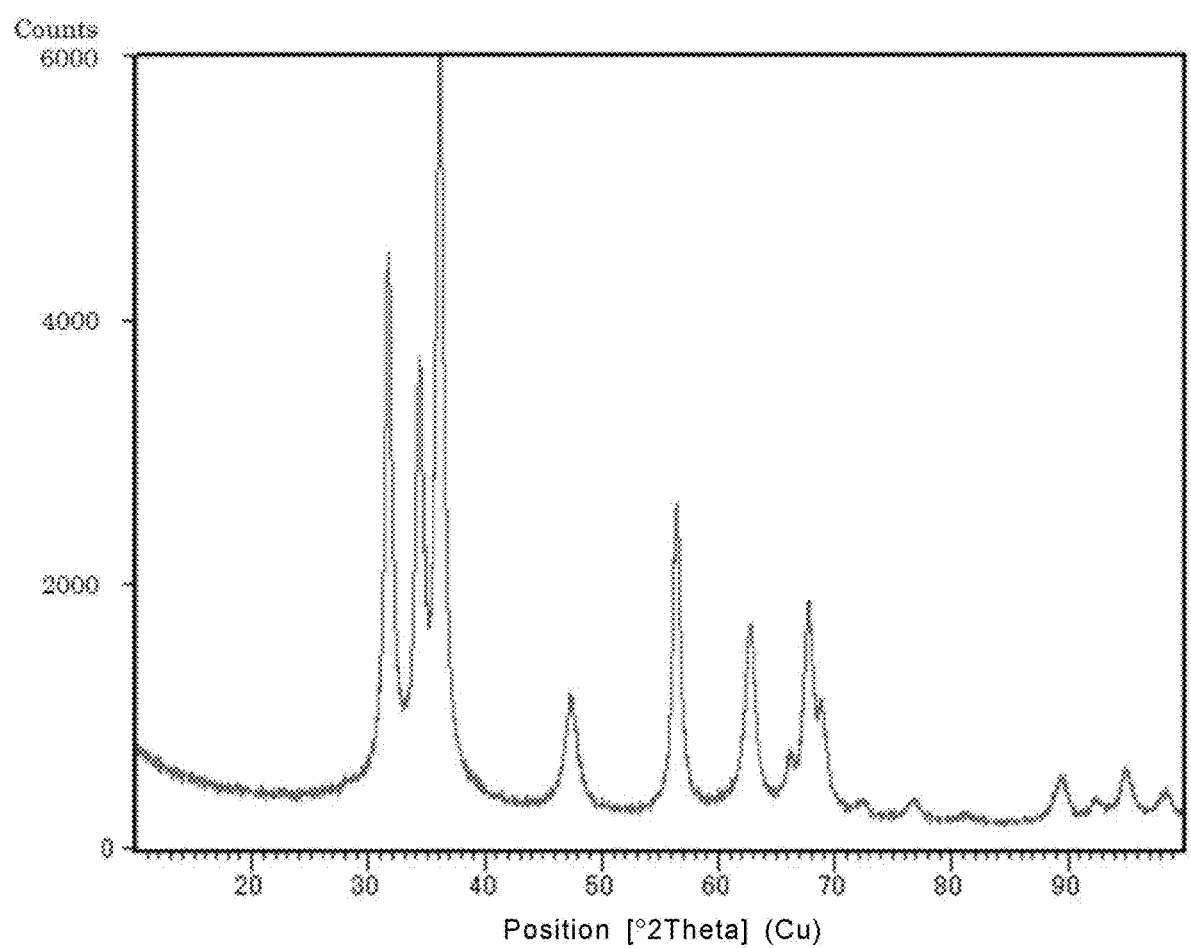
FIG. 3 shows an XRD measurement result of the silicon oxide-coated zinc oxide particles obtained in Example 1 of the present invention.
Figure 4:
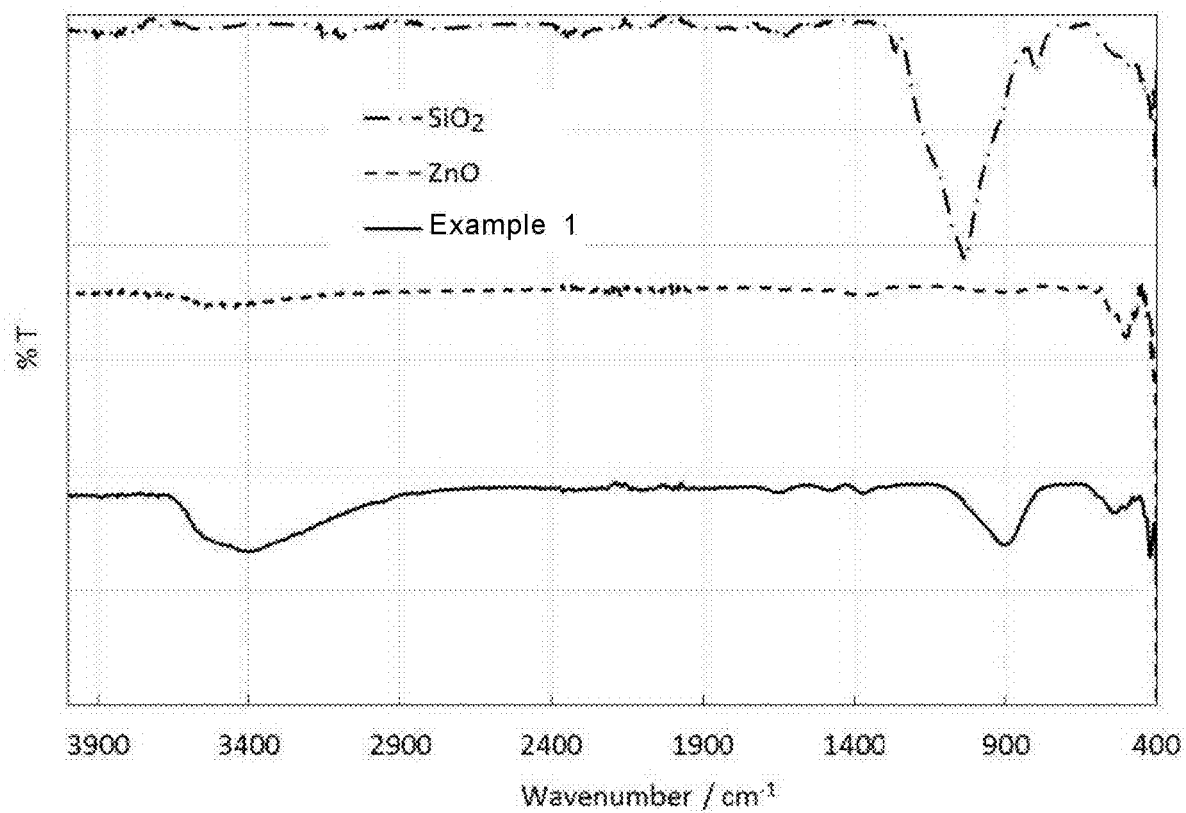
FIG. 4 shows FT-IR measurement results of the silicon oxide-coated zinc oxide particles obtained in Example 1 of the present invention.

FIG. 3 shows an XRD measurement result of the silicon oxide-coated zinc oxide particles obtained in Example 1 as described below. In the measurement result, peaks derived from the zinc oxide (ZnO) are observed, but no other peaks are observed. Further, FIG. 4 shows FT-IR (infrared absorption spectrum) measurement results of the silicon oxide-coated zinc oxide particles obtained in Example 1, together with FT-IR measurement results of silicon dioxide ($SiO_2$) and the zinc oxide (ZnO). As shown in FIG. 4, a broad peak around 900 $cm^{-1}$ was observed for the silicon oxide-coated zinc oxide particles of the present invention. This peak was not observed in the zinc oxide (ZnO), and the wave number of this peak is lower than that of the peak at around 1000 $cm^{-1}$ observed in $SiO_2$. Therefore, it is considered possible that the silicon oxide in the silicon oxide-coated zinc oxide particles obtained in Example 1 is in the state of $SiO_2$ or in the state wherein a part of oxygen is deficient like $SiO_{2-X}$. Further, a broad peak from about 2900 $cm^{-1}$ to about 3600 $cm^{-1}$ derived from hydroxyl groups was observed.

Namely, it can be seen that the silicon oxide-coated zinc oxide particles obtained in Example 1 as described below, are the silicon oxide-coated zinc oxide particles which surface is coated with amorphous silicon oxide.

Figure 5:
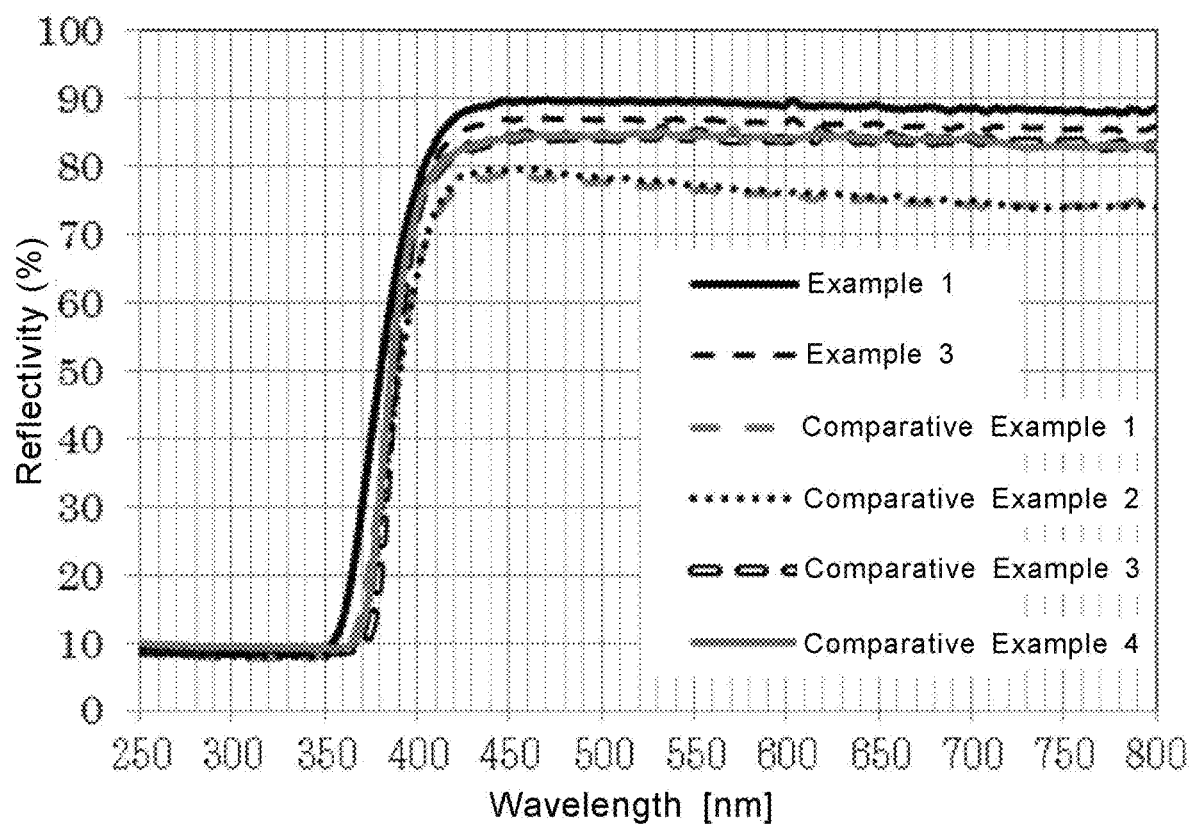
FIG. 5 shows the reflection spectrum measurement results of the silicon oxide-coated zinc oxide particles obtained in Example 1 and Example 3 of the present invention, and of the zinc oxide particles obtained in Comparative Example 1, and of the silicon oxide-coated zinc oxide particles obtained in Comparative Example 2, and of the commercially available zinc oxide particles (Comparative Example 3), and of the commercially available silicon oxide-coated zinc oxide particles (Comparative Example 4) respectively.

FIG. 5 shows the reflection spectra for a wavelength of 250 to 800 nm of the silicon oxide-coated zinc oxide particle powders obtained in Example 1 and Example 3, and of the zinc oxide particle powders which surface is not coated with silicon oxide obtained in Comparative Example 1, and of the silicon oxide-coated zinc oxide particle powders wherein an aggregate of a plurality of zinc oxide particles is coated with silicon oxide obtained in Comparative Example 2, and of the commercially available zinc oxide particles of a particle diameter of 100 to 500 nm (Kanto Chemical Co., Inc., special grade: 3N5, Comparative Example 3), and of the commercially available silicon oxide-coated zinc oxide particles of a particle diameter of 100 to 500 nm (Sakai Chemical Industry Co., Ltd., FINEX –50 W-LP2, Comparative Example 4) respectively. Incidentally, regarding particle size and XRD measurement result of zinc oxide particles, substantially the same results as in Example 1 were obtained to the zinc oxide particles obtained in Comparative Example 1, except that the surface was not coated with silicon oxide, and to the silicon oxide-coated zinc oxide particles obtained in Comparative Example 2, except that an aggregate of a plurality of zinc particles were coated with silicon oxide. Incidentally, transmission spectrum of a dispersion prepared by dispersing the silicon oxide-coated zinc oxide particles obtained in Example 1 and the zinc oxide particles obtained in Comparative Example 1 in propylene glycol at a zinc oxide concentration of 0.015 wt % was measured. As a result, substantially the same results were obtained in the transmission spectrum of the dispersion of Example 1 and the transmission spectrum of the dispersion of Comparative Example 1.

As shown in Table 5, the reflectivity of the silicon oxide-coated zinc oxide particles obtained in Example 1 for the light of the wavelength of around 380 to 780 nm in the visible region, was high as compared with that of the zinc oxide particles obtained in Comparative Example 1. Further, the reflectivity of the silicon oxide-coated zinc oxide particles obtained in Example 2 for the light of the wavelength of around 380 to 780 nm, decreased as compared with that of the silicon oxide-coated zinc oxide particles obtained in Example 1, and was higher than that of the silicon oxide-coated zinc oxide particles obtained in Comparative Example 4 (not shown in FIG). However, significant difference in reflectivity was not observed between the zinc oxide particles of Comparative Example 1 which surface was not coated with silicon oxide, and the aggregate of a plurality of zinc oxide particles coated with silicon oxide having a particle diameter exceeding 100 nm of Comparative Example 2. Further, the reflectivity for the light of the wavelength of 380 to 780 nm of the silicon oxide-coated zinc oxide particles obtained in Example 3 wherein an aggregate of a plurality of zinc oxide particles was coated with silicon oxide which particle diameter was 100 nm or less, was lower than that of Example 1, and was higher than that of the zinc oxide of Comparative Example 1 which surface was not coated with silicon oxide. Further, significant difference in reflectivity was not observed between the commercially available zinc oxide particles of a particle diameter of 100 to 500 nm of Comparative Example 3, and the silicon oxide-coated zinc oxide particles of a particle diameter of 100 to 500 nm of Comparative Example 4. Namely, it was shown that a white light is reflected effectively by coating the surface of zinc oxide with amorphous silicon oxide, and that amorphous silicon oxide coating changes color characteristics, but that the effect on color characteristics decreases when zinc oxide particles exceeding 100 nm, or an aggregate of zinc oxide, particularly an aggregate of zinc oxide particles exceeding 100 nm are coated with silicon oxide. In case of using for a paint a silicon oxide-coated zinc oxide composition for coating containing silicon oxide-coated zinc oxide particles which reflection for a white light is enhanced by coating at least a part of the surface of oxide particles with amorphous silicon oxide, for example, it is suitable to reduce amount of the paint, to enhance ability of expression using color intensity, as well as to enhance designability. In addition, even in case of using for a paint for a coating film for a clear layer, it is possible to enhance its transparency, and the like. Moreover, the silicon oxide-coated zinc oxide composition for coating can be suitably used as a white pigment because the composition reflects almost all region of the visible lights uniformly.

Thus, in case that oxide particles in silicon oxide-coated oxide particles of the present invention are zinc oxide particles, a silicon oxide-coated oxide composition for coating of the present invention includes silicon oxide-coated oxide particles, and the silicon oxide-coated oxide particles are constituted so that reflectivity for the light of 380 to 780 nm is higher than that of oxide particles which surface is not coated with silicon oxide.

Figure 6:
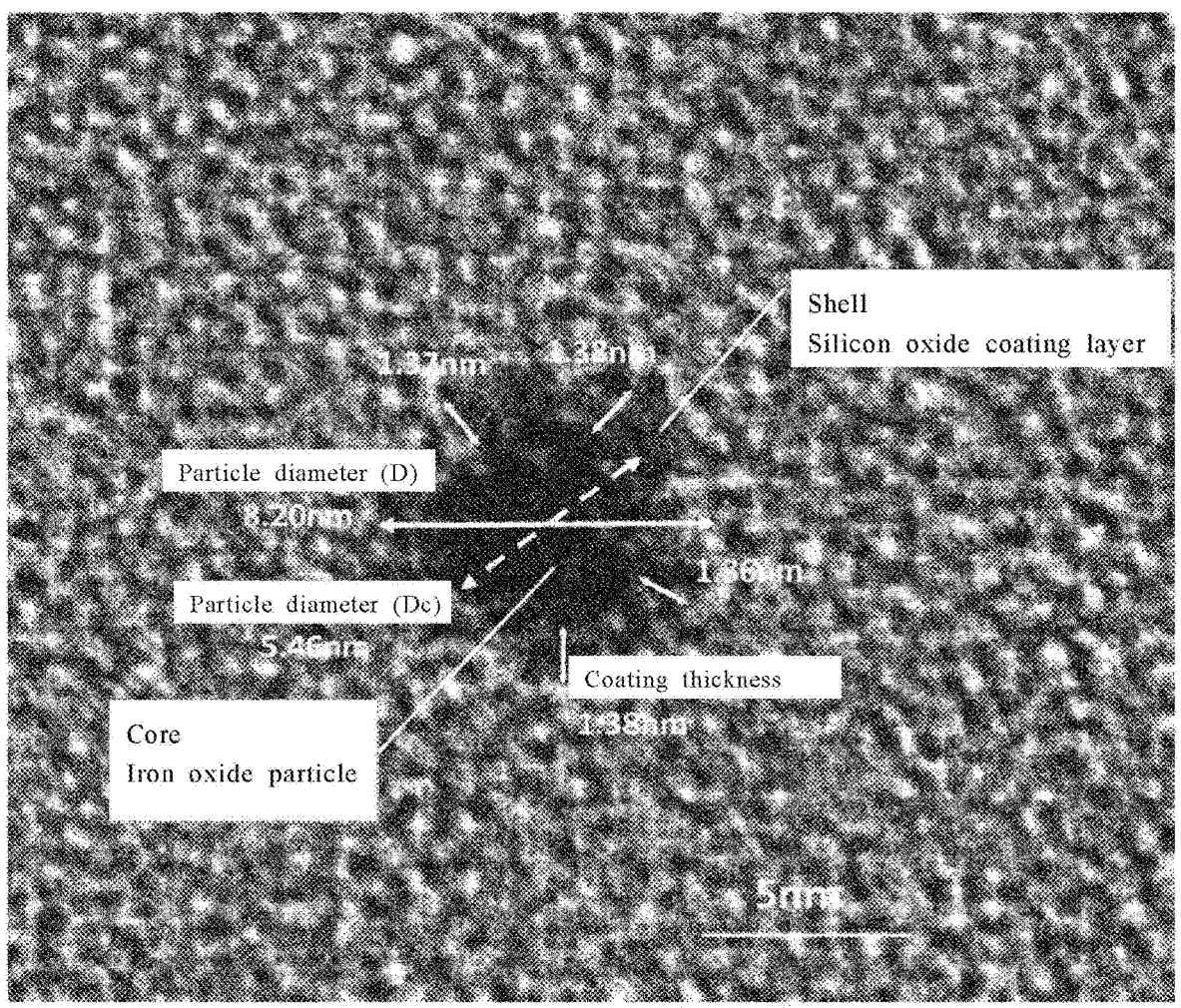
FIG. 6 shows a TEM photograph of the silicon oxide-coated iron oxide particles obtained in Example 4 of the present invention.
Figure 7:
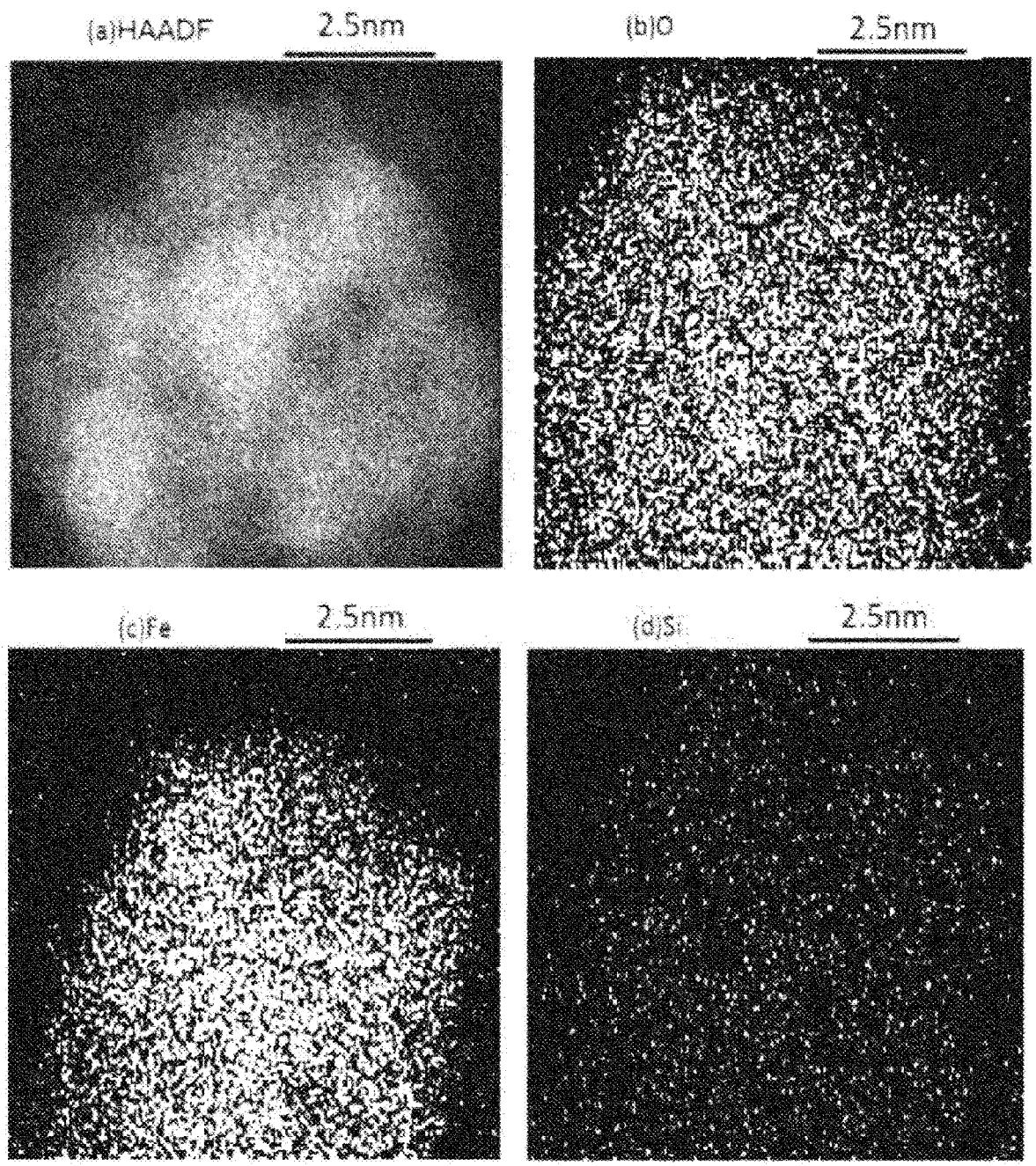
FIG. 7 shows an STEM mapping of the silicon oxide-coated iron oxide particles obtained in Example 4 of the present invention.

FIG. 6 shows a TEM photograph of the iron oxide particles which surface is coated with silicon oxide (hereinafter, referred to as silicon oxide-coated iron oxide particles) obtained in Example 4. As shown in FIG. 6, core-shell type silicon oxide-coated iron oxide particles wherein the core was one iron oxide particle, and the entire surface of the core was uniformly coated with silicon oxide, were observed, and a coating layer (shell) of silicon oxide having a thickness of about 1.37 nm on the entire surface of the core iron oxide particle was observed. FIG. 7 shows a mapping result using STEM of the silicon oxide-coated iron oxide particles obtained in Example 4. In FIG. 7, (a) shows a mapping of a dark-field image (HADDF image), (b) shows a mapping of oxygen (O), (c) shows a mapping of iron (Fe), and (d) shows a mapping of silicon (Si). Regarding the observed particles in the HADDF image, distribution of oxygens (O) and silicons (Si) was observed in the entire particles, and distribution of iron (Fe) was observed in about 1.37 nm smaller area in radius compared with the particles.

Figure 8:
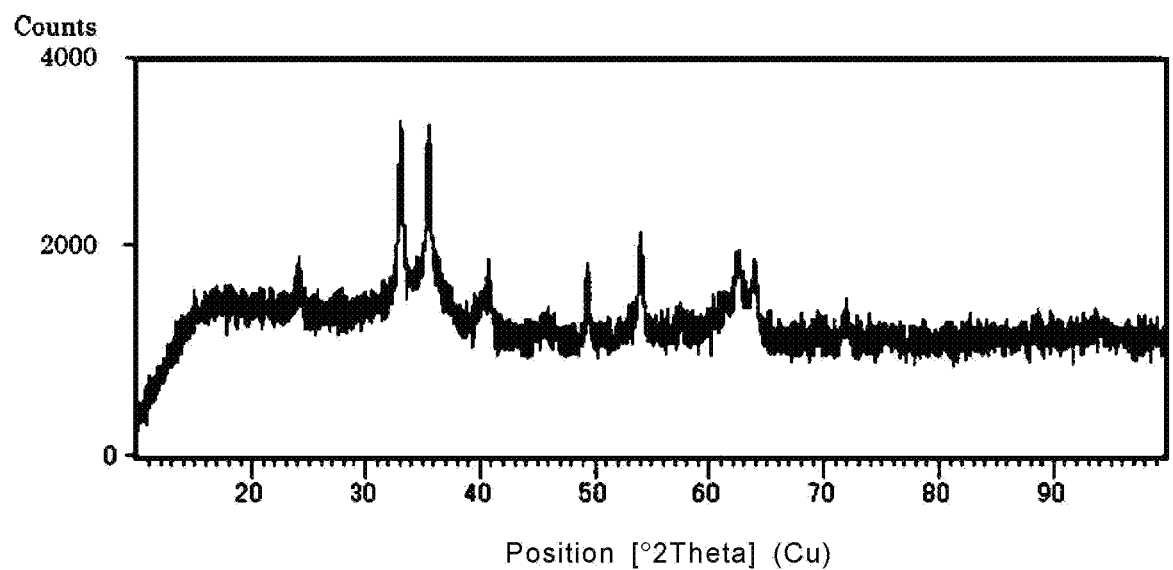
FIG. 8 shows an XRD measurement result of the silicon oxide-coated iron oxide particles obtained in Example 4 of the present invention.
Figure 9:
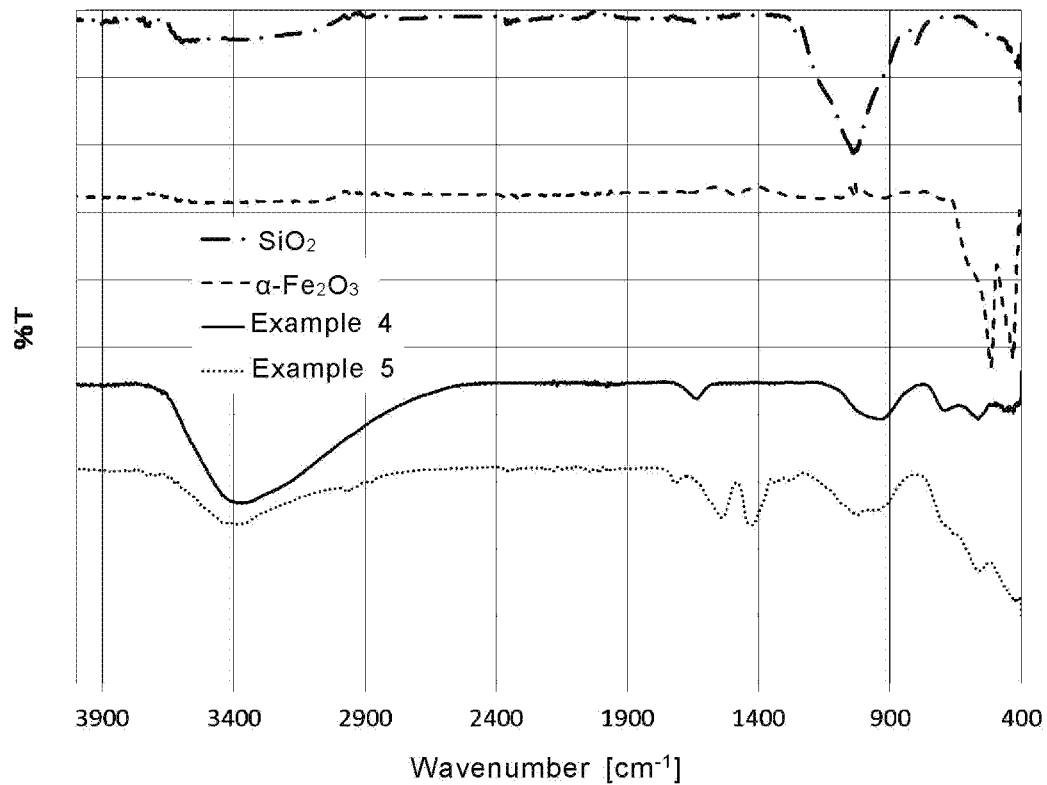
FIG. 9 shows FT-IR measurement results of the silicon oxide-coated iron oxide particles obtained in Example 4 and Example 5 of the present invention.

FIG. 8 shows an XRD measurement result of the silicon oxide-coated iron oxide particles obtained in Example 4 as described below. In the measurement result, peaks derived from the iron oxide ($\alpha$-$Fe_2O_3$) were observed, but no other peaks were observed. Further, FIG. 9 shows FT-IR (infrared absorption spectrum) measurement results of the silicon oxide-coated iron oxide particles obtained in Example 4 and the silicon oxide-coated iron oxide particles obtained in Example 5, wherein the silicon oxide-coated iron oxide particles obtained in Example 4 were provided with acetyl groups, together with FT-IR measurement results of silicon dioxide ($SiO_2$) and the iron oxide ($\alpha$-$Fe_2O_3$). As shown in FIG. 9, a broad peak around 950 $cm^{-1}$ was observed for the silicon oxide-coated iron oxide particles obtained in Example 4. This peak was not observed in the iron oxide ($\alpha$-$Fe_2O_3$), and the wave number of this peak is lower than that of the peak at around 1000 $cm^{-1}$ observed in $SiO_2$. Therefore, it is considered possible that the silicon oxide in the silicon oxide-coated iron oxide particles obtained in Example 4 is in the state of $SiO_2$ or in the state wherein a part of oxygen is deficient like $SiO_{2-X}$. Further, a broad peak from about 2900 $cm^{-1}$ to about 3600 $cm^{-1}$ derived from hydroxyl groups was observed. Also, in the FT-IR measurement result of the silicon oxide-coated iron oxide particles obtained in Example 5 wherein the silicon oxide-coated iron oxide particles obtained in Example 4 were provided with acetyl groups, the broad peak from about 2900 $cm^{-1}$ to about 3600 $cm^{-1}$ derived from hydroxyl groups is smaller, which was observed in the FT-IR measurement result of the silicon oxide-coated iron oxide particles obtained in Example 4, and peaks at about 1450 $cm^{-1}$ and about 1600 $cm^{-1}$ derived from acetyl groups were observed.

Namely, the silicon oxide-coated iron oxide particles obtained in Example 4 as described below is considered to be silicon oxide-coated iron oxide particles which surface is coated with amorphous silicon oxide. And the silicon oxide-coated iron oxide particles obtained in Example 5 is considered to be prepared by addition of an acetyl group to a hydroxyl group contained in the silicon oxide-coated iron oxide particles obtained in Example 4, and to add an acetyl group to the silicon oxide-coated iron oxide particles.

Figure 10:
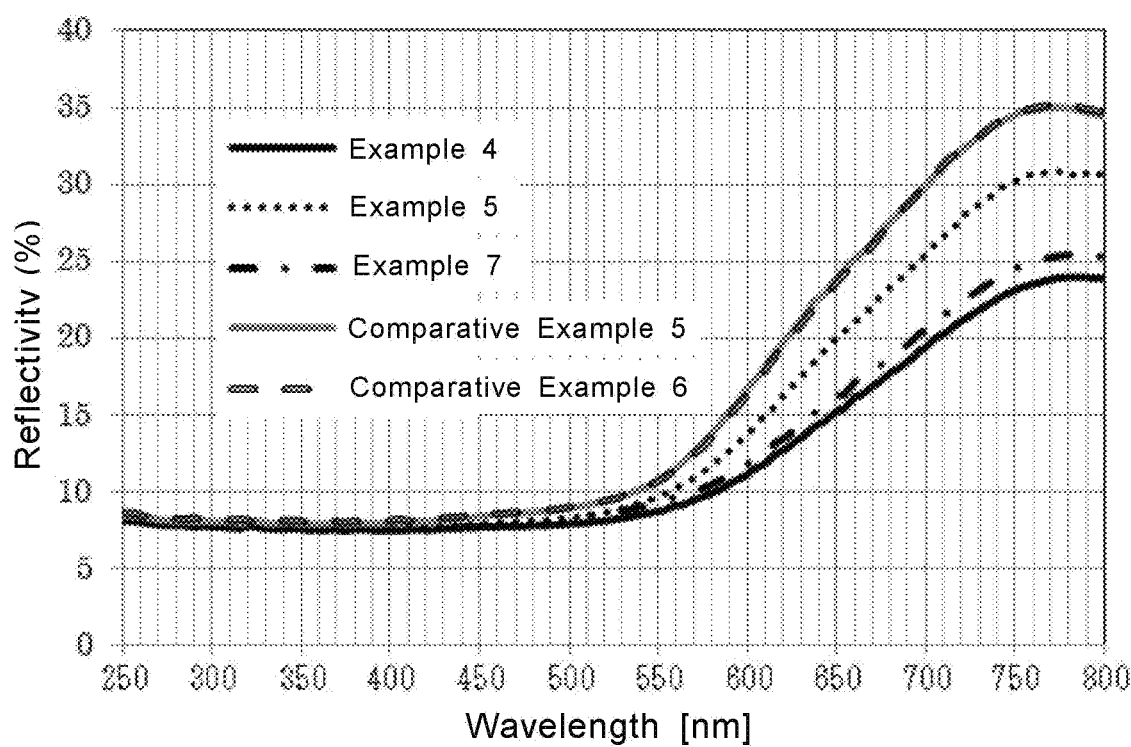
FIG. 10 shows the reflection spectrum measurement results of the silicon oxide-coated iron oxide particles obtained in Example 4, Example 5 and Example 7 of the present invention, and of the iron oxide particles obtained in Comparative Example 5, and of the silicon oxide-coated iron oxide particles obtained in Comparative Example 6 respectively.
Figure 15:
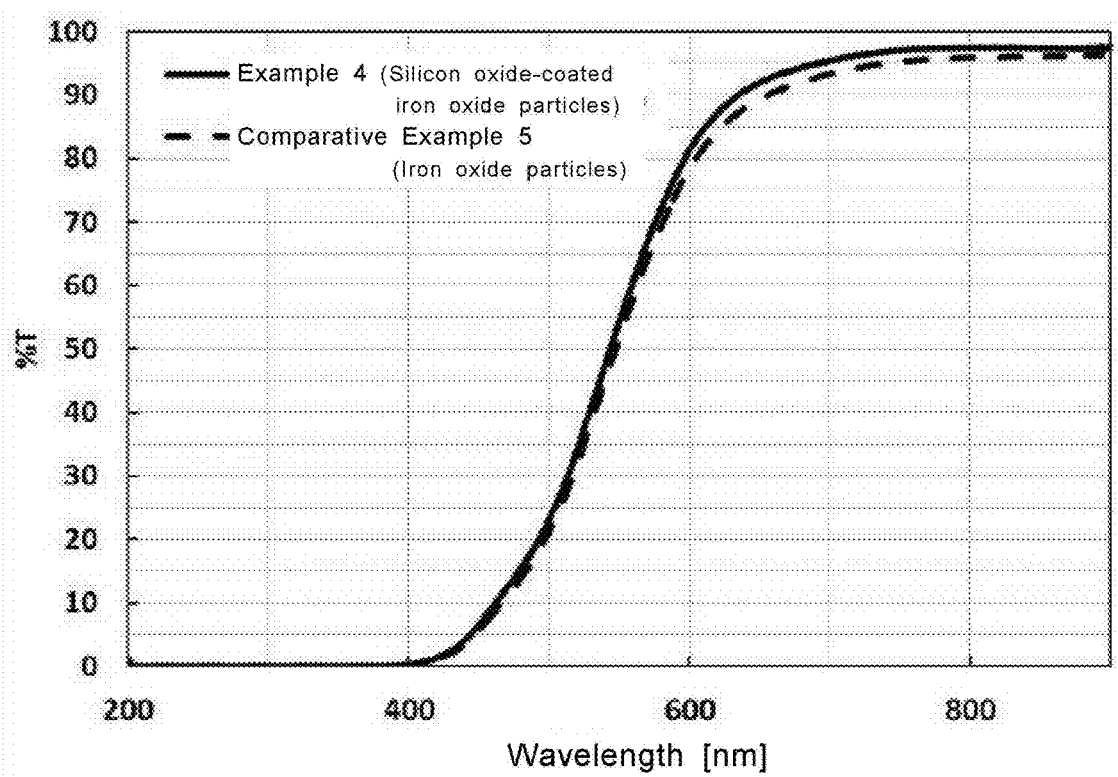
FIG. 15 shows the transmission spectrum of the dispersions in propylene glycol of the silicon oxide-coated iron oxide particles obtained in Example 4 of the present invention, and of the iron oxide particles obtained in Comparative Example 5 respectively.

FIG. 10 shows the reflection spectra for a wavelength of 250 to 800 nm of the silicon oxide-coated iron oxide particle powders obtained in Example 4 and Example 7, and of the iron oxide particle powders which surface is not coated with silicon oxide obtained in Comparative Example 5, and of the silicon oxide-coated iron oxide particle powders provided with acetyl groups obtained in Example 5, and of the silicon oxide-coated iron oxide particle powders wherein an aggregate of a plurality of iron oxide particles is coated with silicon oxide obtained in Comparative Example 6 respectively. Incidentally, regarding particle size and XRD measurement result of iron oxide particles, substantially the same results as in Example 4 were obtained to the iron oxide particles obtained in Comparative Example 5, except that the surface was not coated with silicon oxide, and to the silicon oxide-coated iron oxide particles obtained in Example 5, except addition of an acetyl group to the silicon oxide-coated iron oxide particles, and further to the silicon oxide-coated iron oxide particles obtained in Comparative Example 6, except that an aggregate of a plurality of iron oxide particles was coated with silicon oxide. Incidentally, transmission spectrum of a dispersion prepared by dispersing the silicon oxide-coated iron oxide particles obtained in Example 4 and the iron oxide particles obtained in Comparative Example 5 in propylene glycol at an iron oxide concentration of 0.05 wt % was measured. As a result, substantially the same results were obtained in the transmission spectrum of the dispersion of Example 4 and the transmission spectrum of the dispersion of Comparative Example 5 as shown in FIG. 15. Further, transmission spectrum of a dispersion prepared by dispersing the silicon oxide-coated iron oxide obtained in Example 5 in butyl acetate at an iron oxide concentration of 0.05 wt % was measured. As a result, the measured transmission spectrum was substantially the same as the above transmission spectrum of respective dispersion of Example 4 and Comparative Example 5.

As shown in FIG. 10, the reflectivity of the silicon oxide-coated iron oxide particles obtained in Example 4 for the light of the wavelength of around 550 to 800 nm, was low as compared with that of the iron oxide particles obtained in Comparative Example 5. This shows the result that amorphous silicon oxide coating gives a change in color characteristics. Further, the reflectivity of the silicon oxide-coated iron oxide particles obtained in Example 5 for the light of the wavelength of around 550 to 800 nm, increased as compared with that of the silicon oxide-coated iron oxide particles obtained in Example 4. This shows that the color characteristics change by addition of an acetyl group to the silicon oxide-coated iron oxide particles. This result indicates that the color characteristics change by changing a functional group contained in the particles. Also, the reflectivity of the silicon oxide-coated iron oxide particles obtained in Example 6 for the light of the wavelength of around 550 to 800 nm, decreased as compared with that of the silicon oxide-coated iron oxide particles obtained in Example 5, and was higher than that of the silicon oxide-coated iron oxide particles obtained in Example 4 (not shown in FIG). However, significant difference in reflectivity was not observed between the iron oxide particles which surface is not coated with silicon oxide of Comparative Example 5 and aggregate of a plurality of iron oxide particles coated with silicon oxide of Comparative Example 6. Further, the reflectivity for the light of the wavelength of 550 to 800 nm of the silicon oxide-coated iron oxide particles obtained in Example 7 wherein an aggregate of a plurality of iron oxide particles was coated with silicon oxide, which particle diameter is 50 nm or less, was slightly higher than that of Example 4, and was lower than that of the silicon oxide-coated iron oxide particles as in Comparative Example 6 wherein an aggregate of a plurality of iron oxide particles was coated with silicon oxide, and the particle diameter of the aggregate exceeds 50 nm. It was found that reflectivity could be controlled by a coating condition of the surface of iron oxide particles with silicon oxide. On the other hand, it was found that the effect on color characteristics was lowered when an aggregate of iron oxide particles, particularly an aggregate of iron oxide particles having more than 50 nm diameter was coated with silicon oxide.

For example, in case of being used in a silicon oxide-coated oxide composition for coating of the present invention, the composition can express a deeper red color, when the reflectivity of the silicon oxide-coated iron oxide particles for the light of the wavelength of around 550 to 800 nm is reduced like the silicon oxide-coated iron oxide particles obtained in Example 4. The composition can express a brighter red color, when the reflectivity for the light of the wavelength of around 550 to 800 nm is higher than that of the silicon oxide-coated iron oxide particles obtained in Example 4, like the silicon oxide-coated iron oxide particles obtained in Example 5. Thus, it is possible to use properly silicon oxide-coated iron oxide particles depending on a desired color and designability. Significant color change can be observed by visual inspection.

When the oxide particles in the silicon oxide coating oxide particles of the present invention are iron oxide particles, the silicon oxide-coated oxide composition for coating of the present invention includes silicon oxide-coated oxide particles. The silicon oxide-coated oxide particles of the present invention is constituted so that the reflectivity for the light of the wavelength of around 550 to 800 nm, is reduced as compared with that of the oxide particles without silicon oxide coating. The effects by the above mentioned constitution are the followings in addition to the above mentioned effects. When a silicon oxide-coated oxide composition for coating of the present invention is mixed to a paint for a clear coating film or a paint for a colored coating film to form a coating film, specifically in case that a color of the coated body is recognized by making a light pass through the a clear coating film and a colored coating film, and then by making the light reflected on the base metallic coating film pass through the clear coating film and colored coating film again, the transmittance of the silicon oxide-coated n oxide particles of the present invention contained in the clear coating film and colored coating film for the light of the wavelength of 550 to 800 nm, is preferably higher, but the reflectivity is preferably lower. This is because, when the reflectivity is high, for example, the site which should be seen as a shade in the coating film or the coated body, exhibits a color, and then the effects providing color depth and shadowing to the coating film or coated body is lowered, and difference between highlight (brightness, vividness) and shade (darkness) when a light shines on a coated body, is difficult to be obtained, and the problem that the coating film or coated body looks blurred occurs, which may impair designability of the product.

Further, in case that oxide particles in silicon oxide-coated oxide particles of the present invention are iron oxide particles, a silicon oxide-coated oxide composition for coating of the present invention includes silicon oxide-coated oxide particles, and the silicon oxide-coated oxide particles include a functional group, or an acetyl group in Example 5 of the present application as described below, and are constituted so that reflectivity for the light of 550 to 800 nm is lower than that of oxide particles which surface is not coated with silicon oxide. Further, in case that oxide particles in silicon oxide-coated oxide particles of the present invention are iron oxide particles, a silicon oxide-coated oxide composition for coating of the present invention includes silicon oxide-coated oxide particles, and is constituted so that reflectivity for the light of 550 to 800 nm is lower than that of silicon oxide-coated oxide particles wherein a hydroxyl group contained in the silicon oxide-coated oxide particles is changed to a functional group other than a hydroxyl group or an acetyl group in Example 5 of the present application.

Color characteristics, particularly reflectivity, of oxide particles can be changed by selecting presence or absence of amorphous silicon oxide coating at least a part of the surface of iron oxide particles, and presence or absence of a functional group contained in silicon oxide-coated oxide particles, or acetyl group shown in the following Examples 4 and 5, to manufacture oxide particles.

A functional group contained in silicon oxide-coated oxide particles, refers to a functional group which is at least introduced to or coupled with silicon oxide-coated oxide particles. Color characteristics, specifically reflectivity of silicon oxide-coated oxide particle can be controlled by changing a functional group. A functional group is believed to be present on the surface of the silicon oxide-coated oxide particles, but it may be present inside the silicon oxide-coated oxide particles. The functional group includes hydroxyl group contained in the silicon oxide-coated oxide particles, or a functional group substitutable with the hydroxyl group. A functional group substitutable with the hydroxyl group includes an acyl group such as acetyl group, benzoyl group and the like, an alkyl group such as methyl group, ethyl group and the like, and an alkyl silyl group, an aryl group and the like. Change of a functional group may be change of at least a part of functional groups contained in silicon oxide-coated oxide particles, or it may be change of all functional groups.

In silicon oxide-coated oxide particles of the present invention, the color characteristics of the silicon oxide-coated oxide composition are controlled by presence or absence of the amorphous silicon oxide coating at least a part of the surface of the oxide particles and the coating rate of the amorphous silicon oxide to the surface of the oxide particles. Presence or absence of the amorphous silicon oxide coating at least a part of the surface of the oxide particles and the coating rate of the amorphous silicon oxide to the surface of the oxide particles make greater influences on the reflectivity of the silicon oxide-coated oxide particle powders, than influences on the transmission spectrum of the dispersion wherein silicon oxide-coated iron oxide particles is dispersed in a liquid dispersion medium.

In silicon oxide-coated oxide particles of the present invention, a shape of the particles has smaller effects than the other factors described above, and thus the shape of the particles may be in various shapes. However, a substantially spherical shape is preferable, because the shape enables reduction of birefringence in the paint. Silicon oxide-coated oxide particles of the present invention are preferably substantially spherical particles, wherein a long diameter/short diameter ratio is from 1.0 to 3.0, preferably from 1.0 to 2.5, more preferably from 1.0 to 2.0. Silicon oxide-coated oxide particles of the present invention are preferably silicon oxide-coated oxide particles having a particle diameter of 1 to 100 nm, more preferably silicon oxide-coated oxide particles having a particle diameter of 1 to 50 nm.

(Manufacturing Method: Device)

A method of producing silicon oxide-coated oxide particles wherein at least a part of the surface is coated with silicon oxide of the present invention includes, for example, a method wherein oxide particles are produced in the first microreactor, and at least a part of the surface of the oxide particles are coated with silicon oxide in the subsequent second microreactor; a method wherein oxide particles are produced in a batch vessel under a dilute system and the like, and continuously at least a part of the surface of the oxide particles are coated with silicon oxide under a dilute system, and the like; a method wherein oxide particles are produced by pulverization such as bead mill, and subsequently at least a part of the surface of the oxide particles are coated with silicon oxide under a dilute system, and the like. The apparatus and method as proposed by the present applicant and described in JP 2009-112892 may be also used. The apparatus described in JP 2009-112892 comprises a stirring tank having an inner peripheral surface which cross-section is circular, and a mixing tool attached to the stirring tank with a slight gap to the inner peripheral surface of the stirring tank, wherein the stirring tank comprises at least two fluid inlets and at least one fluid outlet; from one of the fluid inlets, the first fluid to be processed containing one of the reactants among the fluids to be processed is introduced into the stirring tank; from one fluid inlet other than the above inlet, the second fluid to be processed containing one of reactants different from the above reactant is introduced into the stirring tank through a different flow path; at least one of the stirring tank and the mixing tool rotates at a high speed relative to the other to let the above fluids be in a state of a thin film; and in the above thin film, the reactants contained in the first and second fluids to be processed are reacted. JP 2009-112892 further describes that three or more inlet tubes may be provided as shown in FIGS. 4 and 5 to introduce three or more fluids to be processed into the stirring tank.

Further, in the present invention, it is preferable that production of oxide particles is preferably performed at least using a microreactor. It is more preferable to use an apparatus using the same principle as the fluid processing apparatus described in Patent Literature 5, for production of oxide particles and for coating at least a part of the surface of the produced oxide particles with silicon oxide to form silicon oxide-coated oxide particles.

As an example of a method of producing silicon oxide-coated oxide particles of the present invention, it is preferable to use a method of producing silicon oxide-coated oxide particles, wherein oxide particles are precipitated in a mixed fluid of an oxide raw material liquid containing at least a raw material of oxide particles, and an oxide precipitation liquid containing at least oxide precipitation substance for precipitating oxide particles; and the mixed fluid containing the precipitated oxide particles are mixed with a silicon oxide raw material liquid containing at least a raw material of silicon oxide to coat at least a part of the surface of the oxide particles with silicon oxide. Hereinafter, an oxide raw material liquid may be referred to as an oxide raw material liquid for a core, and a silicon oxide raw material liquid may be referred to as an oxide raw material liquid for a shell.

A raw material of oxide particles and a raw material of silicon oxide which are used in production of a silicon oxide-coated oxide particles of the present invention are not particularly limited. Any substances can be used as long as the substances become an oxide or silicon oxide in a manner such as a reaction, crystallization, precipitation or the like. In the present invention, hereinafter, the method above is referred to as precipitation.

A raw material of oxide particles includes, for example, an elemental metal and an elemental non-metal, and a metal compound and a non-metal compound. A metal in the present invention is not particularly limited, but preferably is all metal elements in the chemical periodic table. An inorganic metal in the present invention not particular limited, but preferably includes B, Si, Ge, As, Sb, C, N, O, S, Te, Se, F, Cl, Br, I, At, and the like. Further, these metals or non-metals may be a single element, or may be an alloy composed of a plurality of elements, or a substance containing a metal element and a non-metal element. In the present invention, the above metal compound is referred to as a metal compound. A metal compound or the above non-metal compound is not particularly limited, but preferably includes, for example, a salt, an oxide, a hydroxide, a hydroxide oxide, a nitride, a carbide, a complex, an organic salt, an organic complex, an organic compound of the metal or non-metal, or a hydrate thereof, an organic solvate thereof, and the like. A metal salt or non-metal salt is not particularly limited, but includes a nitrate, a nitrite, a sulfate, a sulfite, a formate, an acetate, a phosphate, a phosphite, a hypophosphite, a chloride, an oxy salt, an acetylacetonate of the metal or non-metal, or a hydrate thereof, an organic solvate thereof and the like. An organic compound includes a metal alkoxide, a non-metal alkoxide, and the like. These metal compounds or non-metal compounds may be used alone, or a mixture of a plurality of these compounds may be used as a raw material of oxide particles.

When oxide particles are zinc oxide particles or iron oxide particles, a raw material of oxide particles includes, for example, an oxide and a hydroxide of zinc or iron, and other compounds such as a salt and an alkoxide of zinc or iron, and their hydrate and the like. The raw material of oxide particles is not particularly limited, but includes, an inorganic compound such as a chloride, nitrate or sulfate of zinc or iron and the like, and an organic compound such as an alkoxy or acetylacetonate of zinc or iron and the like, and the like. Specific examples include, for example, zinc oxide, zinc chloride, zinc nitrate, iron(III) chloride, iron(II) chloride, iron(II) nitrate, iron(III) sulfate, zinc acetylacetonate, iron acetylacetonate and a hydrate thereof and the like. When oxide particles are titan oxide particles, lead oxide particles or cobalt oxide particles, a raw material of oxide particles includes, for example, an oxide and a hydroxide of titan, lead or cobalt, and other compounds such as a salt and an alkoxide of titan, lead or cobalt, and their hydrate and the like. The raw material of oxide particles is not particularly limited, but includes, an inorganic compound such as a chloride, nitrate or sulfate of titan, lead or cobalt and the like, and an organic compound such as an alkoxy or acetylacetonate of titan, lead or cobalt and the like, and the like.

A raw material of silicon oxide includes a silicon oxide, a silicon hydroxide, other compounds such as a silicon salt and a silicon alkoxide, and a hydrate thereof. Not particularly limited, it includes phenyltrimethoxysilane, methyltrimethoxysilane, methyltriethoxysilane, 3-glycidoxypropyltrimethoxysilane, 3-trifluoropropyl-trimethoxysilane, methacryloxypropyltriethoxysilane, tetramethoxysilane (TMOS), tetraethoxysilane (TEOS), and an oligomeric condensate of TEOS, for example, ethyl silicate 40, tetraisopropylsilane, tetrapropoxysilane, tetraisobutoxysilane, tetrabutoxysilane, and a similar material thereof. Further as a raw material of silicon oxide, another siloxane compound, bis (triethoxysilyl)methane, 1,9-bis(triethoxysilyl)nonane, diethoxydichlorosilane, triethoxychlorosilane and the like may be used.

Further, when a raw material of oxide particles or a raw material of silicon oxide is a solid, it is preferable to use a raw material of oxide particles or a raw material of silicon oxide in a molten state, or in a state of being mixed or dissolved in a solvent described below, including a dispersion state. Even when a raw material of oxide particles or a raw materials of silicon oxide is a liquid or gas, it is preferable to use them in a state of being mixed or dissolved in a solvent described below, including a dispersion state. Regarding a raw material of oxide particles, in case of using one raw material of oxide particles, oxide particles containing one element as an element other than oxygen may be produced. Further, regarding one raw material of oxide particles, in case of using a plurality of raw materials of oxide particles, a composite oxide containing a plurality of elements as an element other than oxygen may be produced. Further, the invention can be performed when these oxide raw material liquid and silicon oxide raw material liquid include those in a state of the condition such as dispersion or slurry.

In the present invention, when oxide particles are iron oxide particles, iron oxide particles are preferably α-$Fe_2O_3$ (hematite). Therefore, an iron ion contained in the raw material of oxide particles is preferably $Fe^{3+}$. It is preferable to use a substance that generates $Fe^{3+}$ ion in a solution as a raw material of oxide particles. However, a raw material of oxide particles may be prepared by dissolving a substance producing a $Fe^{2+}$ ion in a solvent, followed by using a means of changing the $Fe^{2+}$ ion to a $Fe^{3+}$ ion by an oxidizing acid such as nitric acid, and the like.

An oxide precipitation substance is not particularly limited as long as the substance can make a raw material of oxide particles contained in an oxide raw material liquid be precipitated as oxide particles, and can make a raw material of silicon oxide contained in an silicon oxide raw material liquid be precipitated as silicon oxide. For example, an acidic substance or a basic substance may be used. It is preferable to use an oxide precipitation substance at least in a state that the substance is mixed, dissolved or molecularly dispersed in a solvent described below.

A basic substance includes a metal hydroxide such as sodium hydroxide and potassium hydroxide, a metal alkoxide such as sodium methoxide and sodium isopropoxide, an amine compound such as triethylamine, diethylaminoethanol and diethylamine, ammonia and the like.

An acidic substance includes an inorganic acid such as aqua regia, hydrochloric acid, nitric acid, fuming nitric acid, sulfuric acid, fuming sulfuric acid, and an organic acid such as formic acid, acetic acid, chloroacetic acid, dichloroacetic acid, oxalic acid, trifluoroacetic acid, trichloroacetic acid and the like.

A solvent used in preparation of an oxide raw material liquid, an oxide precipitation solvent and silicon oxide raw material liquid, includes, for example, water, an organic solvent, or a mixed solvent of a plurality of these solvents. The water includes tap water, ion exchange water, pure water, ultrapure water, RO water and the like. The organic solvent includes, an alcohol solvent, an amide solvent, a ketone solvent, an ether solvent, an aromatic compound solvent, carbon disulfide, an aliphatic compound solvent, a nitrile solvent, a sulfoxide solvent, a halogen compound solvent, an ester solvent, an ionic liquid, a carboxylic acid compound, a sulfonic acid compound and the like. Each of the above solvents may be used alone, or a plurality of them may be mixed and used. An alcohol solvent includes a monohydric alcohol such as methanol and ethanol, a polyol such as ethylene glycol and propylene glycol, and the like. Further, if necessary, the above acidic substance or the above basic substance may be mixed with an oxide raw material liquid or a silicon oxide raw material liquid, as long as it does not adversely affect production of silicon oxide-coated oxide particles.

(Dispersing Agent and the Like)

In the present invention, various dispersing agents or surfactants may be used depending on a purpose or necessity, as long as they do not adversely affect production of silicon oxide-coated oxide particles. Not particularly limited, as a dispersing agent or a surfactant, various generally used commercial products or products, and newly synthesized products and the like may be used. As an example, a dispersing agent such as an anionic surfactant, a cationic surfactant, a nonionic surfactant, and various polymers and the like may be used. These may be used alone or two or more thereof may be used in combination. The surfactant and dispersing agent may be contained in at least one fluid of the oxide raw material liquid, oxide precipitation solvent, and silicon oxide raw material liquid. In addition, the surfactant and dispersing agent may be contained in another fluid different from the oxide raw material liquid, oxide precipitation solvent, and silicon oxide raw material liquid.

A method of changing a functional group contained in silicon oxide-coated oxide particles of the present invention is not particularly limited. It may be performed by dispersing silicon oxide-coated oxide particles in a desired solvent, and adding a substance containing a functional group into the dispersion liquid, followed by a processing such as stirring. It may be also performed by mixing a fluid containing silicon oxide-coated oxide particles and a fluid containing a substance containing a functional group using a microreactor described above.

A substance having a functional group is a substance containing a functional group that can be substituted with a hydroxyl group contained in silicon oxide-coated oxide particles. The examples include an acylating agent such as acetic anhydride and propionic anhydride, a methylation agent such as dimethyl sulfate and dimethyl carbonate, and a silane coupling agent such as chlorotrimethylsilane and methyl trimethoxysilane, and the like.

Not particularly limited, a painting composition which a silicon oxide-coated oxide composition for coating of the present invention may be blended to, may be applied to those described in Patent Literature 6 or 7, and various painting compositions such as a solvent-based paint, a water-based paint. The painting composition may further comprise in addition to various resin components, if necessary, additives such as pigments, dyes, wetting agents, dispersing agents, color separation inhibitors, leveling agents, viscosity modifiers, anti-skinning agents, anti-gelling agents, antifoaming agents, thickeners, anti-sagging agents, antifungal agents, ultraviolet absorbers, film-forming assistant agents, surfactants, if necessary. A resin component includes polyester resins, melamine resins, phenol resins, epoxy resins, vinyl chloride resins, acrylic resins, urethane resins, silicone resins, fluorine resins and the like.

A coated body which a paint containing a silicon oxide-coated oxide composition for coating of the present invention is applied to, may be a single layer coated body composed of a single painting composition, or a multilayer coated body composed of plurality of painting compositions. The painting composition may be performed by adding it to a paint containing a pigment, or to a paint such as a clear paint.

Color of a coated body is not specifically limited, and a silicon oxide coating oxide composition for coating of the present invention may be used for desired hue. A red color such as color having a hue from RP to YR in the Munsell hue circle; a yellow to green color such as a color having a hue from Y to BG in the Munsell hue circle; a blue to purple color such as a color having a hue from B to P in the Munsell hue circle (each of these colors includes a metallic color) may be blended to a paint composition used for a coated body, but the color is not particularly limited to these colors, and may be a color of any hue. As a pigment or dye optionally included in a painting composition, various pigments and dyes may be used, and for example, all pigments and dyes registered in the color index may be used. Among these colors, a pigment or dye constituting a pigment constituting a green color includes, for example, a pigment or dye classified into C. I. Pigment Green; a pigment constituting a blue color includes, for example, a pigment or dye classified into C. I. Pigment Blue; a pigment constituting a white color includes, for example, a pigment or dye classified into C. I. Pigment White; a pigment constituting a yellow color includes, for example, a pigment or dye classified into C. I. Pigment Yellow; a red color includes, for example, a pigment or dye classified into C. I. Pigment Red in the Color Index, a pigment or dye classified into C. I. Pigment Violet or C. I. Pigment Orange in the Color Index, and the like. More specific examples include a quinacridone pigment such as C. I. Pigment Red 122 and C. I. Violet 19; a diketopyrrolopyrrole pigment such as C. I. Pigment Red 254 and C. I. Pigment Orange73; a naphthol pigment such as C. I. Pigment Red 150 and C. I. Pigment Red 170; a perylene pigment such as C. I. Pigment Red 123 and C. I. Pigment Red 179; and an azo pigment such as C. I. Pigment Red 144, and the like. These pigments and dyes may be used alone, or a plurality of these may be mixed and used. Silicon oxide-coated oxide composition of the present invention may be also mixed in a paint composition alone without mixing with the above pigments and dyes and the like.

EXAMPLE

Hereinafter, the present invention is explained in more detail with reference to Examples, but the present invention is not limited only to these examples.

Incidentally, Comparative Examples 2, 4 and 6 correspond to examples for the inventions according to claims 1 to 2, 4 and 7 of the present application.

Example 1

The oxide raw material liquid for core, the oxide precipitation solvent, and the oxide raw material liquid for shell were prepared using the high-speed rotary dispersion emulsification apparatus CLEAMIX (product name: CLM-2.2 S, M. Technique Co., Ltd.). Specifically, based on the formulation of the oxide raw material liquid for core shown in Example 1 of Table 1, the components of the oxide raw material liquid for core were mixed homogeneously by stirring using CLEARMIX at preparation temperature of 40° C. and at the rotor rotational speed of 20000 rpm for 30 min to prepare the oxide raw material liquid for core. Based on the formulation of the oxide precipitation solvent shown in Example 1 of Table 1, the components of the oxide precipitation solvent were mixed homogeneously by stirring using CLEARMIX at preparation temperature of 45° C. and at the rotor rotational speed of 15000 rpm for 30 min to prepare the oxide precipitation solvent. Furthermore, based on the formulation of the oxide raw material liquid for shell shown in Example 1 of Table 1, the components of the oxide raw material liquid for shell were mixed homogeneously by stirring using CLEARMIX at preparation temperature of 20° C. and at the rotor rotational speed of 6000 rpm for 10 min to prepare the oxide raw material liquid for shell.

Regarding the substances represented by the chemical formula and abbreviations set forth in Table 1, MeOH is methanol (Godo Co.,Ltd.), 97 wt % $H_2SO_4$ is concentrated sulfuric acid (Kishida Chemical Co., Ltd.), KOH is potassium hydroxide (Nippon Soda Ltd.), 35 wt % HCl is hydrochloric acid (Kanto Chemical Co., Inc.), TEOS is tetraethyl orthosilicate (Wako Pure Chemical Industry Ltd.), and ZnO is zinc oxide (Kanto Chemical Co., Inc.).

Then, the prepared oxide raw material liquid for core, the oxide precipitation solvent oxide and the oxide raw material liquid for shell were mixed using the fluid processing apparatus described in Patent Literature 5 filed by the present applicant. Here, the fluid processing apparatus described in Patent Literature 5 is an apparatus described in FIG. 1(B) of Patent Literature 5, wherein the openings d20 and d30 of the second and third introduction parts have concentric annular shapes which are surrounding the central opening of the processing surface 2 which is a ring-shaped disc. Specifically, the oxide precipitation solvent as liquid A was introduced from the first introduction part d1 into the space between the processing surfaces 1 and 2, and while driving the processing member 10 at a rotational speed of 1130 rpm, the oxide raw material liquid for core as liquid B was introduced from the second introduction part d2 into the space between the processing surfaces 1 and 2, and the oxide precipitation solvent and the oxide raw material liquid for core were mixed in the thin film fluid, to let the core oxide particles be precipitated in the space between the processing surfaces 1 and 2. Then, the oxide raw material liquid for shell as liquid C was introduced from the third introduction part d3 into the space between the processing surfaces 1 and 2, and liquid C was mixed with a mixed fluid containing the core oxide particles in the thin film fluid. As a result, silicon oxide was precipitated on the surface of the core oxide particles. The fluid containing the silicon oxide-coated oxide particles (hereinafter, the silicon oxide-coated oxide particle dispersion liquid) was discharged from the space between the processing surfaces 1 and 2 of the fluid processing apparatus. The silicon oxide-coated oxide particle dispersion liquid was collected in the beaker b through the vessel v.

Table 2 shows the operating conditions of the fluid processing apparatus. The introduction temperatures (liquid sending temperatures) and the introduction pressures (liquid sending pressures) of liquid A, liquid B and liquid C shown in Table 2 were measured using a thermometer and a pressure gauge provided in a sealed inlet path leading to the space between the processing surfaces 1 and 2 (the first introduction part d1, the second introduction part d2 and the third introduction part d3). The introduction temperature of liquid A shown in Table 2 is the actual temperature of liquid A under the introduction pressure in the first introduction part d1. Similarly, the introduction temperature of liquid B shown in Table 2 is the actual temperature of liquid B under the introduction pressure in the second introduction part d2. The introduction temperature of liquid C shown in Table 2 is the actual temperature of liquid C under the introduction pressure in the third introduction part d3.

For the pH measurement, the pH meter, model number D-51 manufactured by HORIBA Ltd. was used. The pH of liquid A, liquid B and liquid C were measured at room temperature prior to introduction into the fluid processing apparatus. Further, it is difficult to measure the pH of the mixed fluid immediately after mixing the oxide raw material liquid for core and the oxide precipitation solvent, and the pH of the mixed fluid immediately after mixing the mixed fluid containing the core oxide particles and the oxide raw material liquid for shell. Therefore, the silicon oxide-coated oxide particle dispersion liquid was discharged from the apparatus and collected in a beaker b, and the pH of the liquid was measured at room temperature.

Dry powders and wet cake samples were produced from the silicon oxide-coated oxide particle dispersion liquid which was discharged from the fluid processing apparatus, and collected in the beaker. The manufacturing method was conducted according to a conventional method of this type of processing. The discharged silicon oxide-coated oxide particle dispersion liquid was collected, and the silicon oxide-coated oxide particles were settled, and the supernatant was removed. Thereafter, the silicon oxide-coated oxide particles were washed and settled three times repetitively with the mixed solvent of 100 parts by weight of pure water and 100 parts by weight of methanol, and then, were washed and settled three times repetitively with pure water. A part of the finally obtained wet cake of the silicon oxide-coated oxide particles was dried at 25° C. at −0.10 MPaG for 20 hours to obtain the dry powders. The rest was the wet cake sample.

(Preparation of TEM Observation Sample and Preparation of STEM Observation Sample)

A part of the wet cake samples of the silicon oxide-coated oxide particles after the washing process obtained in Examples was dispersed in propylene glycol, and further was diluted to 100-fold by isopropyl alcohol (IPA). The resulting diluted liquid was dropped to a collodion membrane or a micro grid, and dried to prepare a TEM observation sample or an STEM observation sample.

(Transmission Electron Microscopy and Energy Dispersive X-ray Analyzer: TEM-EDS Analysis)

For observation and quantitative analysis of the silicon oxide-coated iron oxide particles by TEM-EDS analysis, the transmission electron microscopy JEM-2100 (JEOL Ltd.) equipped with the energy dispersive X-ray analyzer JED-2300 (JEOL Ltd.) was used. The observation condition was the acceleration voltage of 80 kV, and the observation magnification of 10,000 times or more. The particle diameters (D) described in Tables 2, 4, 8 and 10 and below were calculated from the maximum distance between two points on the outer periphery of the silicon oxide-coated oxide particles, and the average value of the measured particle diameters of 100 particles was shown. Also the core particle diameter (Dc) described in Tables 2 and 8 and below were primary particle diameters of the oxide particles, and were calculated from the maximum distance between two points on the outer periphery of the core oxide particles in the silicon oxide-coated oxide particles, and the average value of the measured core particle diameters of 100 particles was shown. Also EDS analysis on one particle was performed, and a molar ratio of respective oxides was calculated by conversion from a molar ratio between the elements contained in the core oxide particles and the elements contained in the shell silicon oxide, and the average value of 10 particles was shown. The thickness of the shell silicon oxide (hereinafter referred to as the thickness of the shell layer) was measured. Four thickness was measured for one particle, and the average value of the measured thickness of 10 particles was described in the item "coating thickness" in Table 2 or Table 8, and below. Hereinafter, the core oxide particles are also referred to as a core, and the shell silicon oxide is also referred to as a shell or a shell layer.

(Scanning Transmission Electron Microscopy and Energy Dispersive X-ray Analyzer: STEM-EDS Analysis)

For the mapping and quantification of elements contained in the silicon oxide-coated oxide particles by STEM-EDS analysis, the atomic resolution analytical electron microscopy JEM-ARM200F (JEOL Ltd.) equipped with the energy dispersive X-ray analyzer Centurio (JEOL Ltd.) was used. The observation condition was the acceleration voltage of 80 kV and the observation magnification of 50,000 times or more, and a beam diameter of 0.2 nm was used for analysis.

(X-ray Diffraction Measurement)

For the X-ray diffraction (XRD) measurement, the powder X-ray diffractometer Empyrean (Spectris Co., Ltd., PANalytical Division) was used. The measurement condition was measurement range of 10 to 100 [°2Theta], Cu anticathode, tube voltage of 45 kV, tube current of 40 mA, and scanning speed of 0.3°/min. The XRD was measured using the dry powder of the silicon oxide-coated oxide particles obtained in each Example.

(FT-IR Measurement)

For the FT-IR measurement, the Fourier transform infrared spectrophotometer FT/IR-4100 (JASCO Corporation) was used. The measurement condition was the resolution of 4.0 cm$^{-1}$ and accumulated number of 1024 times, using an ATR method.

(Reflection Spectrum)

For the reflection spectrum, the ultraviolet-visible-near infrared spectrophotometer (product name: SolidSpec-3700, Shimadzu Corporation) was used. Measurement range was 250 to 800 nm, and the sampling rate was 2.0 nm, and the measurement speed was medium speed, and measurement method was a double beam photometry. Total reflection measurement for measuring diffuse reflection and specular reflection was performed. For a background measurement (baseline) in measuring powders, the standard white plate (product name: Spectralon™, Labsphere Inc.) was used. The reflection spectrum was measured using the dry powders of the silicon oxide-coated oxide particles in each Example.

TABLE 1

| Example 1 | | | | | | | | | | |
|---|---|---|---|---|---|---|---|---|---|---|
| Formulation of First fluid (Liquid A) (Oxide precipitation solvent) | | | | | Formulation of Second fluid (Liquid B) (Oxide raw material liquid for core) | | | | | |
| Formulation [wt %] | | | | | Formulation [wt %] | | | | | |
| Raw material | [wt %] | Raw material | [wt %] | pH | Raw material | [wt %] | Raw material | [wt %] | Raw material | [wt %] | pH | pH [° C.] |
| MeOH | 93.70 | 97 wt % H$_2$SO$_4$ | 6.30 | <1 | — | ZnO | 3.00 | KOH | 46.60 | water | 50.40 | >14 | — |

TABLE 1-continued

Example 1

Formulation of Third fluid (Liquid C)
(Oxide raw material liquid for shell)

Formulation [wt %]

| Raw material | [wt %] | Raw material | [wt %] | Raw material | [wt %] | pH | pH [° C.] |
|---|---|---|---|---|---|---|---|
| MeOH | 93.69 | 35 wt % HCl | 5.11 | TEOS | 1.20 | <1 | — |

TABLE 2

Example 1

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 450 | 40 | 95 | 28 | 22 | 25 | 0.050 | 0.10 | 0.10 | 13.29 | 28.1 |

| Coating thickness [nm] | Shell/Core SiO$_2$/ZnO Molar ratio | | Particle diameter (D) [nm] | Core particle diameter (Dc) [nm] | D/Dc |
|---|---|---|---|---|---|
| | Calcurated value | EDS | | | |
| 1.82 | 0.37 | 0.37 | 20.10 | 16.46 | 122.1% |

The molar ratios (shell/core) described in Table 2 and Table 4 are the ratio of the oxides of the elements, which the molar ratio of the elements calculated by the TEM-EDS analysis on one silicon oxide-coated oxide particle is converted into. For example, the molar ratio (shell/core, SiO$_2$/ZnO) in Example 1 of Table 2 is the value of SiO$_2$/ZnO converted from the molar ratio of Si/Zn calculated by with TEM-EDS analysis on one silicon oxide-coated oxide particle. Table 2 shows the average molar ratio (SiO$_2$/ZnO) of 10 particles together with its calculated value. The calculated value was calculated from the Zn concentration in the oxide raw material liquid for core and its introduction flow rate, and the Si concentration in the oxide raw material liquid for shell and its introduction flow rate.

FIG. 1 shows a TEM photograph of the silicon oxide-coated oxide particles obtained in Example 1. Core-shell type silicon oxide-coated zinc oxide particles wherein the core was one zinc oxide particle, and the entire surface of the core was uniformly coated with silicon oxide, were observed, and a coating layer (shell) of silicon oxide having a thickness of about 1.8 nm on the entire surface of the core zinc oxide particle was observed. FIG. 2 shows a mapping result using STEM of the silicon oxide-coated zinc oxide particles obtained in Example 1. In FIG. 2, (a) shows a mapping of a dark-field image (HADDF image), (b) shows a mapping of oxygen (O), (c) shows a mapping of zinc (Zn), and (d) shows a mapping of silicon (Si). Regarding the observed particles in the HADDF image, distribution of oxygens (O) and silicons (Si) was observed in the entire particles, and distribution of zinc (Zn) was observed in about 1.8 nm smaller area in radius compared with the particles. D/Dc was 122.1%.

FIG. 3 shows the XRD measurement result of the silicon oxide-coated zinc oxide particles obtained in Example 1. In the measurement result, peaks derived from the zinc oxide (ZnO) were observed, but no other peaks were observed. Further, FIG. 4 shows FT-IR (infrared absorption spectrum) measurement results of the silicon oxide-coated zinc oxide particles obtained in Example 1, together with FT-IR measurement results of silicon dioxide (SiO$_2$) and zinc oxide (ZnO). As shown in FIG. 4, a broad peak around 900 cm$^{-1}$ was observed for the silicon oxide-coated zinc oxide particles obtained in Example 1. This peak was not observed in the zinc oxide (ZnO), and the wave number of this peak is lower than that of the peak at around 1000 cm$^{-1}$ observed in SiO$_2$. Therefore, it is considered possible that the silicon oxide in the silicon oxide-coated zinc oxide particles obtained in Example 1 is in the state of SiO$_2$ or in the state wherein a part of oxygen is deficient like SiO$_{2-x}$. Further, a broad peak from about 2900 cm$^{-1}$ to about 3600 cm$^{-1}$ derived from hydroxyl groups was observed.

Comparative Example 1

In Comparative Example 1, the zinc oxide particles which surface was not coated by silicon oxide was prepared in the same manner as in Example 1 except that the oxide raw material liquid for shell as liquid C was not used (except the liquid C condition). TEM observation, reflection spectrum and XRD were measured in a similar manner as in Example 1. The particle diameter measured by the same method as for the core particle diameter in Example 1 was 19.8 nm. From the XRD measurement result, only the peak of zinc oxide was detected. The pH of the discharged liquid was 13.36 (measurement temperature 28.2° C.). The resulting zinc oxide particles in the zinc oxide particle dispersion liquid had already been aggregated.

Example 2

In Example 2, the silicon oxide-coated zinc oxide particles were prepared in the same manner as in Example 1 except for using an apparatus described in JP 2009-112892, and using a method of mixing and reacting liquid A (oxide precipitation solvent), liquid B (oxide raw material liquid for core) and liquid C (oxide raw material liquid for shell). Here, the apparatus of JP 2009-112892 is an apparatus described in FIG. 4 of JP 2009-112892, wherein the inner diameter of the stirring tank is uniform and is 420 mm, and the gap between the outer end of the mixing tool and the inner peripheral surface of the stirring tank is 1 mm, and the rotor rotational speed of the stirring blade was the same as the rotor rotational speed (1130 rpm) of the processing member 10 in the fluid processing apparatus used in Example 1. Further, liquid A was introduced into the stirring tank, and liquid B was added, mixed and reacted in the thin film consisting of liquid A that was crimped to the inner peripheral surface of the stirring tank. Then, liquid C was added, mixed and reacted in the thin film consisting of the mixed liquid of liquid A and liquid B crimped to the inner peripheral surface of the stirring tank. As a result of TEM observation, the core was one zinc oxide particle, and the silicon oxide-coated zinc oxide particles wherein a part of the surface of the core was coated with silicon oxide, was observed. A coating layer (shell) of silicon oxide having a thickness of from 2.0 nm to 3.0 nm on the surface of the core zinc oxide particle was observed. A mapping using STEM of the silicon oxide-coated zinc oxide particles obtained in Example 2, was done in the same manner as in Example 1. Regarding the observed particles in the HADDF image, distribution of oxygens (O) was observed in the entire particles, and distribution of zinc (Zn) was observed in about 2.0 nm to 3.0 nm smaller area in radius compared with the particles, and distribution of silicons (Si) was observed mainly in the coating layers. The particle diameter (D) was 33.6 nm, the thickness of shell silicon oxide (coating thickness) was from 2.0 nm to 3.0 nm, and D/Dc of the silicon oxide-coated zinc oxide particles was from 111.9% to 117.9%. From the XRD measurement results of the silicon oxide-coated zinc oxide particles in Example 2, peaks derived from zinc oxide (ZnO) were observed, and no other peaks were observed.

Example 3

The oxide raw material liquid for core, the oxide precipitation solvent, and the oxide raw material liquid for shell were prepared using the high-speed rotary dispersion emulsification apparatus CLEAMIX (product name: CLM-2.2 S, M. Technique Co., Ltd.). Specifically, based on the formulation of the oxide raw material liquid for core shown in Example 3 of Table 3, the components of the oxide raw material liquid for core were mixed homogeneously by stirring using CLEARMIX at preparation temperature of 40° C. and at the rotor rotational speed of 20000 rpm for 30 min to prepare the oxide raw material liquid for core. Based on the formulation of the oxide precipitation solvent shown in Example 3 of Table 3, the components of the oxide precipitation solvent were mixed homogeneously by stirring using CLEARMIX at preparation temperature of 45° C. and at the rotor rotational speed of 15000 rpm for 30 min to prepare the oxide precipitation solvent. Furthermore, based on the formulation of the oxide raw material liquid for shell shown in Example 3 of Table 3, the components of the silicon oxide raw material liquid were mixed homogeneously by stirring using CLEARMIX at preparation temperature of 20° C. and at the rotor rotational speed of 6000 rpm for 10 min to prepare the oxide raw material liquid for shell.

Regarding the substances represented by the chemical formula and abbreviations set forth in Table 3, MeOH is methanol (Godo Co., Ltd.), 97 wt % $H_2SO_4$ is concentrated sulfuric acid (Kishida Chemical Co., Ltd.), KOH is potassium hydroxide (Nippon Soda Ltd.), 35 wt % HCl is hydrochloric acid (Kanto Chemical Co., Inc.), TEOS is tetraethyl orthosilicate (Wako Pure Chemical Industry Ltd.), and ZnO is zinc oxide (Kanto Chemical Co., Inc.).

TABLE 3

| Example 3 | | | | | | | | | | |
|---|---|---|---|---|---|---|---|---|---|---|
| Formulation of First fluid (Liquid A) (Oxide precipitation solvent) | | | | | Formulation of Second fluid (Liquid B) (Oxide raw material liquid for core) | | | | | |
| Formulation [wt %] | | | | | Formulation [wt %] | | | | | |
| Raw material | [wt %] | Raw material | [wt %] | pH | pH [° C.] | Raw material | [wt %] | Raw material | [wt %] | Raw material | [wt %] | pH | pH [° C.] |
| MeOH | 93.70 | 97 wt % $H_2SO_4$ | 6.30 | <1 | — | ZnO | 3.00 | KOH | 46.60 | Pure water | 50.40 | >14 | — |
| Formulation of Third fluid (Liquid C) (Oxide raw material liquid for shell) | | | | | | | |
| Formulation [wt %] | | | | | | | |
| Raw material | [wt %] | Raw material | [wt %] | Raw material | [wt %] | pH | pH [° C.] |
| MeOH | 94.04 | 35 wt % HCl | 4.16 | TEOS | 1.80 | <1 | — |

TABLE 4

Example 3

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 900 | 80 | 150 | 28 | 24 | 25 | 0.108 | 0.20 | 0.25 | 13.41 | 27.9 |

| Coating thickness [nm] | Shell/Core SiO$_2$/Fe$_2$O$_3$ Molar ratio | | Particle diameter (D) [nm] | Core particle diameter (Dc) [nm] | D/Dc |
|---|---|---|---|---|---|
| | Calcurated value | EDS | | | |
| — | 0.44 | 0.46 | 43.50 | 32.14 | 135.3% |

Figure 13:
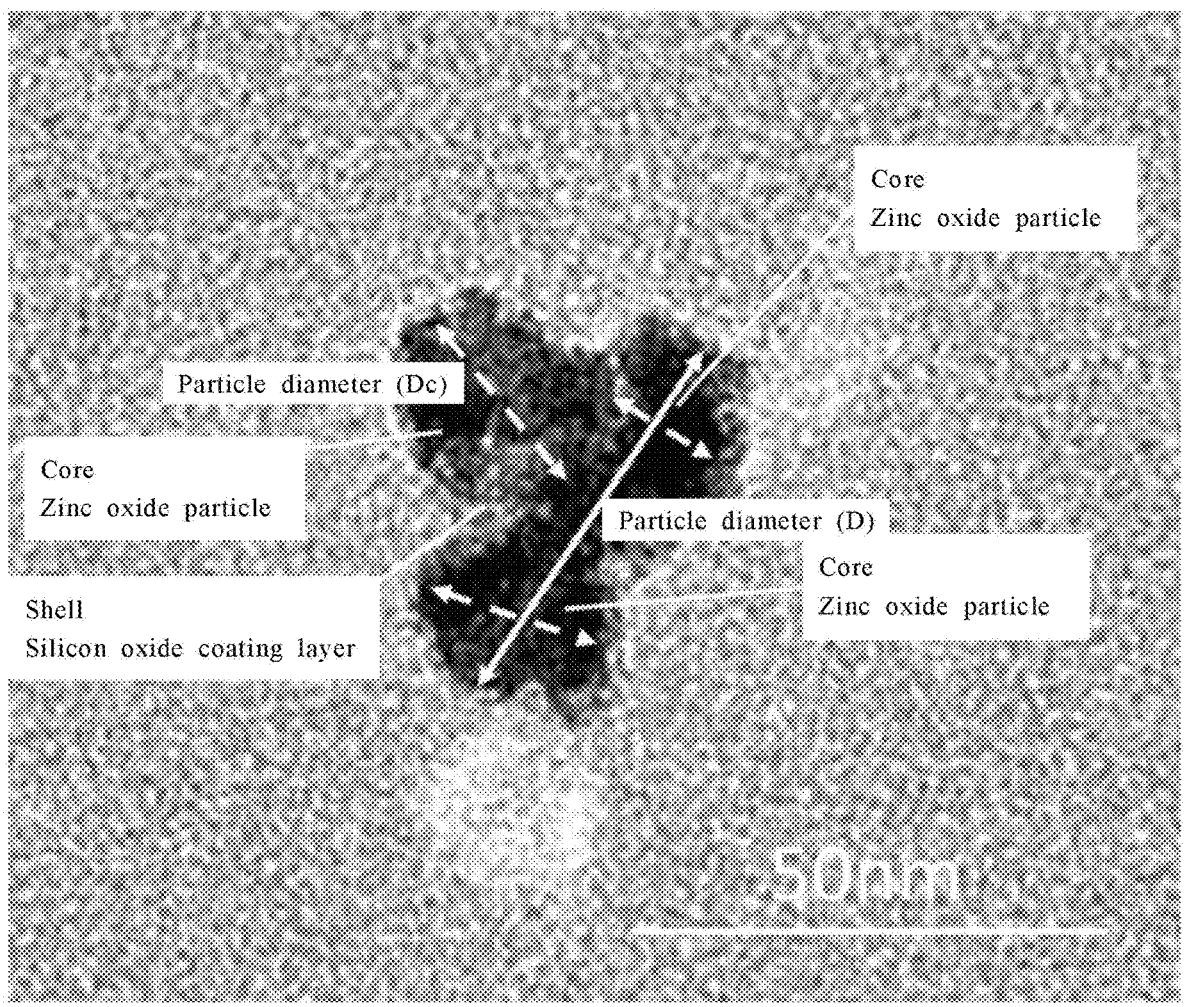
FIG. 13 shows a TEM photograph of the silicon oxide-coated zinc oxide particles obtained in Example 3 of the present invention.

Then, the prepared oxide raw material liquid for core, the oxide precipitation solvent, and the oxide raw material liquid for shell were mixed in the same fluid processing apparatus as in Example 1. Table 4 shows the operating conditions of the fluid processing apparatus. The core conversion particle diameter (Dc) described in Table 4 is the maximum distance between two points on the outer periphery of the aggregate formed by the core zinc oxide particles, and the average value of the measured diameters of 100 aggregates is shown. The methods of washing, analysis and evaluation of particles are the same as in Example 1. By the TEM photograph of the silicon oxide-coated oxide particles obtained in Example 3, zinc oxide particles in which the entire surface of one zinc oxide particle was coated uniformly with silicon oxide as obtained in Example 1 were not observed, but many particles in which the surface of an aggregate of a plurality of zinc oxide particles was coated with silicon oxide were observed. A TEM photograph of the silicon oxide-coated oxide particles obtained in Example 3 is shown in FIG. 13. As shown in FIG. 13, it was observed that the surface of a core aggregate of primary zinc oxide particles was coated with shell silicon oxide. Further, the particle diameter of the silicon oxide-coated zinc oxide particles obtained in Example 3 was 100 nm or less. In the XRD measurement results, peaks of zinc oxide were detected as in Example 1, and the FT-IR measurement results were similar to those in Example 1. The particle diameter D was 43.5 nm, the thickness of shell silicon oxide (coating thickness) was 0.5 to 2.0 nm, and D/Dc of the silicon oxide-coated zinc oxide was about 135.3%.

Comparative Example 2

The oxide raw material liquid for core, the oxide precipitation solvent, and the oxide raw material liquid for shell were prepared using the high-speed rotary dispersion emulsification apparatus CLEAMIX (product name: CLM-2.2 S, M. Technique Co., Ltd.). Specifically, based on the formulation of the oxide raw material liquid for core shown in Comparative Example 2 of Table 5, the components of the oxide raw material liquid for core were mixed homogeneously by stirring using CLEARMIX at preparation temperature of 40° C. and at the rotor rotational speed of 20000 rpm for 30 min to prepare the oxide raw material liquid for core. Based on the formulation of the oxide precipitation solvent shown in Comparative Example 2 of Table 5, the components of the oxide precipitation solvent were mixed homogeneously by stirring using CLEARMIX at preparation temperature of 45° C. and at the rotor rotational speed of 15000 rpm for 30 min to prepare the oxide precipitation solvent. Furthermore, based on the formulation of the oxide raw material liquid for shell shown in Comparative Example 2 of Table 5, the components of the oxide raw material liquid for shell were mixed homogeneously by stirring using CLEARMIX at preparation temperature of 20° C. and at the rotor rotational speed of 6000 rpm for 10 min to prepare the oxide raw material liquid for shell.

Regarding the substances represented by the chemical formula and abbreviations set forth in Table 5, MeOH is methanol (Godo Co., Ltd.), 60 wt % HNO$_3$ is concentrated nitric acid (Kishida Chemical Co., Ltd.), KOH is potassium hydroxide (Nippon Soda Ltd.), 35 wt % HCl is hydrochloric acid (Kanto Chemical Co., Inc.), TEOS is tetraethyl orthosilicate (Wako Pure Chemical Industry Ltd.), and ZnO is zinc oxide (Kanto Chemical Co., Inc.).

TABLE 5

Comparative Example 2

| Formulation of First fluid (Liquid A) (Oxide precipitation solvent) | | | | | | Formulation of Second fluid (Liquid B) (Oxide raw material liquid for core) | | | | | | | |
|---|---|---|---|---|---|---|---|---|---|---|---|---|---|
| Formulation [wt %] | | | | | | Formulation [wt %] | | | | | | | |
| Raw material | [wt %] | Raw material | [wt %] | pH | pH [° C.] | Raw material | [wt %] | Raw material | [wt %] | Raw material | [wt %] | pH | pH [° C.] |
| MeOH | 99.65 | 60 wt % HNO$_3$ | 0.35 | 0.5 | 26.3 | ZnO | 0.50 | KOH | 4.56 | Pure water | 94.94 | 13.7 | 26.1 |

TABLE 5-continued

Comparative Example 2

Formulation of Third fluid (Liquid C)
(Oxide raw material liquid for shell)

Formulation [wt %]

| Raw material | [wt %] | Raw material | [wt %] | Raw material | [wt %] | pH | pH [° C.] |
|---|---|---|---|---|---|---|---|
| Pure water | 97.305 | 35 wt % HCl | 2.560 | TEOS | 0.135 | 0.9 | 25.7 |

TABLE 6

Comparative Example 2

| Introduction flow rate [ml/mm] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 450 | 38 | 40 | 36 | 27 | 25 | 0.015 | 0.10 | 0.10 | 12.62 | 28.4 |

Figure 11:
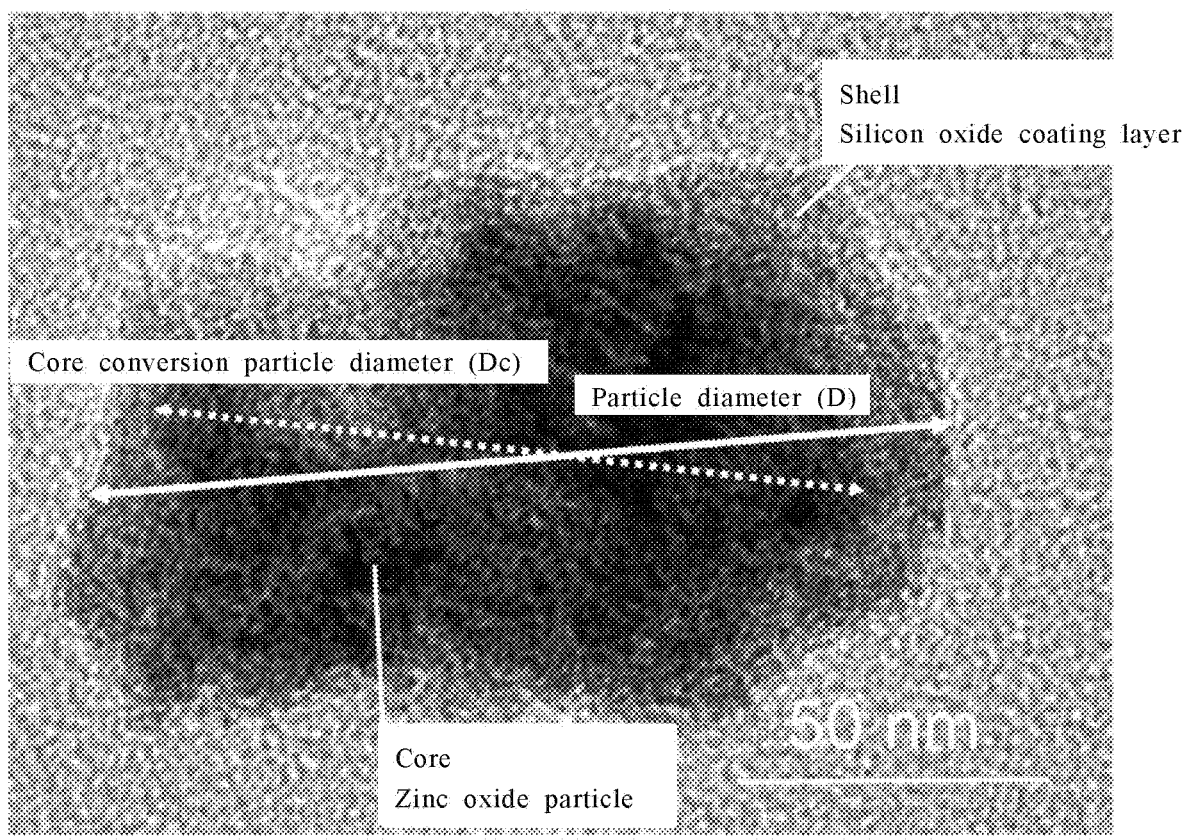
FIG. 11 shows a TEM photograph of the silicon oxide-coated zinc oxide particles obtained in Comparative Example 2 of the present invention.

Then, the prepared oxide raw material liquid for core, the oxide precipitation solvent, and the oxide raw material liquid for shell were mixed in the same fluid processing apparatus as in Example 1. Table 6 shows the operating conditions of the fluid processing apparatus. The methods of washing, analysis and evaluation of particles are the same as in Example 1. As a result of TEM observation of the silicon oxide-coated oxide particles obtained in Comparative Example 2, zinc oxide particles wherein the entire surface of one zinc oxide particle is uniformly coated with silicon oxide, were not observed, and many particles wherein an aggregate of a plurality of zinc oxide particles is coated with silicon oxide were observed. FIG. 11 shows a TEM photograph of the silicon oxide-coated oxide particles obtained in Comparative Example 2. As shown in FIG. 11, it is observed that the core aggregate of primary particles of zinc oxide is coated with shell silicon oxide. The particles wherein a core primary particle of zinc oxide cannot be recognized are also observed. Further, the particle diameter of the zinc oxide aggregate in the silicon oxide-coated zinc oxide particles obtained in Comparative Example 2, exceeds 100 nm. In the XRD measurement results, peaks of zinc oxide were detected as in Example 1, and the FT-IR measurement results were similar to those in Example 1.

Commercially available zinc oxide particles of a particle diameter of 100 to 500 nm (Kanto Chemical Co., Inc., special grade: 3N5) are Comparative Example 3, and commercially available silicon oxide-coated zinc oxide particles of a particle diameter of 100 to 500 nm (Sakai Chemical Industry Co., Ltd., FINEX -50 W-LP2) are Comparative Example 4.

FIG. 5 shows the reflection spectra for a wavelength of 250 to 800 nm of the silicon oxide-coated zinc oxide particle powders obtained in Example 1 and Example 3, and of the zinc oxide particle powders which surface is not coated with silicon oxide obtained in Comparative Example 1, and of the silicon oxide-coated zinc oxide particle powders wherein an aggregate of a plurality of zinc oxide particles is coated with silicon oxide obtained in Comparative Example 2, and of the commercially available zinc oxide particles of a particle diameter of 100 to 500 nm (Kanto Chemical Co., Inc., special grade: 3N5, Comparative Example 3), and of the commercially available silicon oxide-coated zinc oxide particles of a particle diameter of 100 to 500 nm (Sakai Chemical Industry Co., Ltd., FINEX −50 W-LP2, Comparative Example 4) respectively. Incidentally, transmission spectrum of a dispersion prepared by dispersing the silicon oxide-coated zinc oxide obtained in Example 1 and the zinc oxide obtained in Comparative Example 1 in propylene glycol at a zinc oxide concentration of 0.015 wt % was measured. As a result, substantially the same results were obtained in the transmission spectrum of the dispersion of Example 1 and the transmission spectrum of the dispersion of Comparative Example 1.

As shown in Table 5, the reflectivity of the silicon oxide-coated zinc oxide particles obtained in Example 1 for the light of the wavelength of around 380 to 780 nm in the visible region, was high as compared with that of the zinc oxide particles obtained in Comparative Example 1. Further, the reflectivity of the silicon oxide-coated zinc oxide particles obtained in Example 2 for the light of the wavelength of around 380 to 780 nm, decreased as compared with that of the silicon oxide-coated zinc oxide particles obtained in Example 1, and was higher than that of the silicon oxide-coated zinc oxide particles obtained in Comparative Example 4 (not shown in FIG). However, significant difference in reflectivity was not observed between the zinc oxide particles of Comparative Example 1 which surface was not coated with silicon oxide, and the aggregate of a plurality of zinc oxide particles coated with silicon oxide having a particle diameter exceeding 100 nm of Comparative Example 2. Further, the reflectivity for the light of the wavelength of 380 to 780 nm of the silicon oxide-coated zinc oxide particles obtained in Example 3 wherein an aggregate of a plurality of zinc oxide particles was coated with silicon oxide which particle diameter was 100 nm or less, was lower than that of Example 1, and was higher than that of the zinc oxide of Comparative Example 1 which surface was not coated with silicon oxide. Further, significant difference in reflectivity was not observed between the commercially available zinc oxide particles of a particle diameter of 100 to 500 nm of Comparative Example 3, and the commercially available silicon oxide-coated zinc oxide particles of a particle diameter of 100 to 500 nm of Comparative Example 4. Namely, it was shown that a white light is reflected effectively by coating the surface of zinc oxide with amorphous silicon oxide, and that amorphous silicon oxide coating changes color characteristics, but that the effect on color characteristics decreases when zinc oxide particles exceeding 100 nm, or an aggregate of zinc oxide, particularly an aggregate of zinc oxide particles exceeding 100 nm are coated with silicon oxide. In case of using for a paint a silicon oxide-coated zinc oxide composition for coating containing silicon oxide-coated zinc oxide particles which reflection of a white light is enhanced by coating with silicon oxide, for example, it is suitable to reduce amount of the paint, to enhance ability of expression using color intensity, as well as to enhance designability. In addition, even in case of using for a paint for a coating film for a clear coating film, it is possible to enhance its transparency, and the like.

Example 4

The oxide raw material liquid for core, the oxide precipitation solvent, and the oxide raw material liquid for shell were prepared using the high-speed rotary dispersion emulsification apparatus CLEAMIX (product name: CLM-2.2 S, M. Technique Co., Ltd.). Specifically, based on the formulation of the oxide raw material liquid for core shown in Example 4 of Table 7, the components of the oxide raw material liquid for core were mixed homogeneously by stirring using CLEARMIX at preparation temperature of 40° C. and at the rotor rotational speed of 20000 rpm for 30 min to prepare the oxide raw material liquid for core. Based on the formulation of the oxide precipitation solvent shown in Example 4 of Table 7, the components of the oxide precipitation solvent were mixed homogeneously by stirring using CLEARMIX at preparation temperature of 45° C. and at the rotor rotational speed of 15000 rpm for 30 min to prepare the oxide precipitation solvent. Furthermore, based on the formulation of the oxide raw material liquid for shell shown in Example 4 of Table 7, the components of the silicon oxide raw material liquid were mixed homogeneously by stirring using CLEARMIX at preparation temperature of 20° C. and at the rotor rotational speed of 6000 rpm for 10 min to prepare the oxide raw material liquid for shell.

Regarding the substances represented by the chemical formula and abbreviations set forth in Table 7, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.).

Then, the prepared oxide raw material liquid for core, the oxide precipitation solvent oxide and the oxide raw material liquid for shell were mixed using the fluid processing apparatus described in Patent Literature 5 filed by the present applicant. Here, the fluid processing apparatus described in Patent Literature 5 is an apparatus described in FIG. 1(B) of Patent Literature 5, wherein the openings d20 and d30 of the second and third introduction parts have concentric annular shapes which are surrounding the central opening of the processing surface 2 which is a ring-shaped disc. Specifically, the oxide raw material liquid for core as liquid A was introduced from the first introduction part d1 into the space between the processing surfaces 1 and 2, and while driving the processing member 10 at a rotational speed of 1130 rpm, the oxide precipitation solvent as liquid B was introduced from the second introduction part d2 into the space between the processing surfaces 1 and 2, and the oxide raw material liquid for core and the oxide precipitation solvent were mixed in the thin film fluid, to let the core oxide particles be precipitated in the space between the processing surfaces 1 and 2. Then, the oxide raw material liquid for shell as liquid C was introduced from the third introduction part d3 into the space between the processing surfaces 1 and 2, and liquid C was mixed with a mixed fluid containing the core oxide particles in the thin film fluid. Silicon oxide was precipitated on the surface of the core oxide particles. The discharge liquid containing the silicon oxide-coated oxide particles (hereinafter, the silicon oxide-coated oxide particle dispersion liquid) was discharged from the space between the processing surfaces 1 and 2 of the fluid processing apparatus. The silicon oxide-coated oxide particle dispersion liquid was collected in the beaker b through the vessel v. The methods of washing, analysis and evaluation of particles are the same as in Example 1.

Table 8 shows the operating conditions of the fluid processing apparatus. The introduction temperatures (liquid sending temperatures) and the introduction pressures (liquid sending pressures) of liquid A, liquid B and liquid C shown in Table 8 were measured using a thermometer and a pressure gauge provided in a sealed inlet path leading to the space between the processing surfaces 1 and 2 (the first introduction part d1, the second introduction part d2 and the third introduction part d3). The introduction temperature of liquid A shown in Table 8 is the actual temperature of liquid A under the introduction pressure in the first introduction part d1. Similarly, the introduction temperature of liquid B is the actual temperature of liquid B under the introduction pressure in the second introduction part d2. The introduction temperature of liquid C is the actual temperature of liquid C under the introduction pressure in the third introduction part d3.

TABLE 7

| Example 4 | | | | | | | | | | |
|---|---|---|---|---|---|---|---|---|---|---|
| Formulation of First fluid (Liquid A) (Oxide raw material liquid for core) | | | | | Formulation of Second fluid (Liquid B) (Oxide precipitation solvent) | | | | | |
| Formulation [wt %] | | | | | Formulation [wt %] | | | | | |
| Raw material | [wt %] | Raw material | [wt %] | pH | pH [° C.] | Raw material | [wt %] | Raw material | [wt %] | pH | pH [° C.] |
| $Fe(NO_3)_3$ $9H_2O$ | 2.00 | Pure water | 98.00 | 1.8 | 26.6 | NaOH | 9.00 | Pure water | 91.00 | >14 | — |

TABLE 7-continued

Example 4

Formulation of Third fluid (Liquid C)

Formulation [wt %]

| Raw material | [wt %] | Raw material | [wt %] | Raw | [wt %] | pH | pH [° C.] |
|---|---|---|---|---|---|---|---|
| Pure water | 92.89 | 97 wt % $H_2SO_4$ | 5.11 | TEOS | 2.00 | <1 | — |

TABLE 8

Example 4

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 400 | 50 | 100 | 142 | 86 | 89 | 0.451 | 0.50 | 0.50 | 12.14 | 32.9 |

| Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|
| | Calcurated value | EDS | | | |
| 1.37 | 0.97 | 0.97 | 8.20 | 5.46 | 150.2% |

The molar ratios (shell/core) described in Table 8 and Table 10 are the ratio of the oxides of the elements, which the molar ratio of the elements calculated by the TEM-EDS analysis on one silicon oxide-coated oxide particle is converted into. For example, the molar ratio (shell/core, $SiO_2/Fe_2O_3$) in Example 4 of Table 8 is the value of $SiO_2/Fe_2O_3$ converted from the molar ratio of Si/Fe calculated by with TEM-EDS analysis on one silicon oxide-coated oxide particle. Table 8 shows the average molar ratio ($SiO_2/Fe_2O_3$) of 10 particles together with its calculated value. The calculated value was calculated from the Fe concentration in the oxide raw material liquid for core and its introduction flow rate, and the Si concentration in the oxide raw material liquid for shell and its introduction flow rate.

FIG. 6 shows a IBM photograph of the silicon oxide-coated oxide particles obtained in Example 4. Core-shell type silicon oxide-coated iron oxide particles wherein the core was one iron oxide particle, and the entire surface of the core was uniformly coated with silicon oxide, were observed, and a coating layer (shell) of silicon oxide having a thickness of about 1.37 nm on the entire surface of the core iron oxide particle was observed. FIG. 7 shows a mapping result using STEM of the silicon oxide-coated iron oxide particles obtained in Example 4. In FIG. 7, (a) shows a mapping of a dark-field image (HADDF image), (b) shows a mapping of oxygen (O), (c) shows a mapping of iron (Fe), and (d) shows a mapping of silicon (Si). Regarding the observed particles in the HADDF image, distribution of oxygens (O) and silicons (Si) was observed in the entire particles, and distribution of iron (Fe) was observed in about 1.37 nm smaller area in radius compared with the particles. D/Dc was 150.2%.

Example 5

The following process was performed to impart acetyl groups to the silicon oxide-coated iron oxide particles obtained in Example 4. First, 1 part by weight of the silicon oxide-coated iron oxide particles obtained in Example 4 was added to 99 parts by weight of propylene glycol, and dispersed using the high-speed rotary dispersion emulsification apparatus CLEARMIX (product name: CLM-2.2 S, M technique Co., Ltd.) at 65° C. at the rotor rotation speed of 20000 rpm for 1 hour, to prepare a dispersion. To the obtained propylene glycol dispersion of the silicon oxide-coated iron oxide particles, were added 2 parts by weight of pyridine and 1 part by weight of acetic anhydride relative to 1 part by weight of the silicon oxide-coated iron oxide particles, and were dispersed using the above high-speed rotary dispersion emulsification apparatus at 65° C. at a rotor rotational speed of 20000 rpm for 1 hour. The resulting processed liquid was centrifuged at the condition of 26,000 G for 15 min, and the supernatant was separated to obtain the precipitates. A part of the precipitates was dried at −0.10 MPaG at 25° C. for 20 hours to obtain the dried powders. As a result of TEM observation, the core particle diameter (Dc) of the silicon oxide-coated iron oxide particles obtained in Example 5 was 5.47 nm, and the particle diameter (D) was 8.19 nm. Thus, it was confirmed that the particle diameter was substantially the same to that in Example 4. D/Dc was 149.7%.

In the XRD measurement result of the silicon oxide-coated iron oxide particles obtained in Example 4 as shown in FIG. 8, peaks derived from the iron oxide ($\alpha$-$Fe_2O_3$) were observed, but no other peaks were observed. The XRD measurement results of the silicon oxide-coated iron oxide particles obtained in Example 5 were similar to those of the silicon oxide-coated iron oxide particles in Example 4. Further, FIG. 9 shows FT-IR (infrared absorption spectrum) measurement results of the silicon oxide-coated iron oxide particles obtained in Example 4 and the silicon oxide-coated iron oxide particles obtained in Example 5 wherein the silicon oxide-coated iron oxide particles obtained in Example 4 were provided with acetyl groups, together with FT-IR measurement results of silicon dioxide ($SiO_2$) and an iron oxide ($\alpha$-$Fe_2O_3$). As shown in FIG. 9, a broad peak around 950 $cm^{-1}$ was observed for the silicon oxide-coated iron oxide particles obtained in Example 4. This peak was not observed in the iron oxide ($\alpha$-$Fe_2O_3$), and the wave number of this peak is lower than that of the peak at around 1000 $cm^{-1}$ observed in $SiO_2$. Therefore, it is considered possible that the silicon oxide in the silicon oxide-coated iron oxide particles obtained in Example 4 is in the state of $SiO_2$ or in the state wherein a part of oxygen is deficient like $SiO_{2-X}$. Further, a broad peak from about 2900 $cm^{-1}$ to about 3600 $cm^{-1}$ derived from hydroxyl groups was observed. Also, in the FT-IR measurement result of the silicon oxide-coated iron oxide particles obtained in Example 5 wherein the silicon oxide-coated iron oxide particles obtained in Example 4 were provided with acetyl groups, the broad peak from about 2900 $cm^{-1}$ to about 3600 $cm^{-1}$ derived from hydroxyl groups is smaller, which was observed in the FT-IR measurement result of the silicon oxide-coated iron oxide particles obtained in Example 4, and peaks at about 1450 $cm^{-1}$ and about 1600 $cm^{-1}$ derived from acetyl groups were observed.

Namely, the silicon oxide-coated iron oxide particles obtained in Example 4 is a silicon oxide-coated iron oxide particles which surface is coated with amorphous silicon oxide. And the silicon oxide-coated iron oxide particles obtained in Example 5 is considered to be prepared by addition of an acetyl group to the silicon oxide-coated iron oxide particles obtained in Example 4 by replacing a hydroxyl group contained in the silicon oxide-coated iron oxide particles with an acetyl group.

Comparative Example 5

In Comparative Example 5, the iron oxide particles which surface was not coated by silicon oxide was prepared in the same manner as in Example 4 except that the oxide raw material liquid for shell as liquid C was not used (except the liquid C condition). TEM observation, reflection spectrum and XRD were measured in a similar manner as in Example 4. The particle diameter measured by the same method as for the core particle diameter in Example 4 was 6.40 nm. From the XRD measurement result, only the peak of iron oxide was detected. The pH of the discharged liquid was 13.89 (measurement temperature 29.6° C.). The resulting iron oxide particles in the iron oxide particle dispersion liquid had already been aggregated.

Example 6

In Example 6, the silicon oxide-coated iron oxide particles were prepared in the same manner as in Example 4 except for using an apparatus described in JP 2009-112892, and using a method of mixing and reacting liquid A (oxide raw material liquid for core), liquid B (oxide precipitation solvent) and liquid C (oxide raw material liquid for shell). Here, the apparatus of JP 2009-112892 is an apparatus described in FIG. 4 of JP 2009-112892, wherein the inner diameter of the stirring tank is uniform and is 420 mm, and the gap between the outer end of the mixing tool and the inner peripheral surface of the stirring tank is 1 mm, and the rotor rotational speed of the stirring blade was the same as the rotor rotational speed (1130 rpm) of the processing member 10 in the fluid processing apparatus used in Example 4. Further, liquid A was introduced into the stirring tank, and liquid B was added, mixed and reacted in the thin film consisting of liquid A that was crimped to the inner peripheral surface of the stirring tank. Then, liquid C was added, mixed and reacted in the thin film consisting of the mixed liquid of liquid A and liquid B crimped to the inner peripheral surface of the stirring tank. As a result of TEM observation, the core was one iron oxide particle, and the silicon oxide-coated iron oxide particles wherein a part of the surface of the core was coated with silicon oxide, was observed. A coating layer (shell) of silicon oxide having a thickness of from 1.0 nm to 2.0 nm on the surface of the core iron oxide particle was observed. A mapping using STEM of the silicon oxide-coated iron oxide particles obtained in Example 6, was done in the same manner as in Example 4. Regarding the observed particles in the HADDF image, distribution of oxygens (O) was observed in the entire particles, and distribution of iron (Fe) was observed in about 1.0 nm to 2.0 nm smaller area in radius compared with the particles, and distribution of silicons (Si) was observed mainly in the coating layers. The particle diameter (D) was 16.9 nm, the thickness of shell silicon oxide (coating thickness) was from 1.0 nm to 2.0 nm, and D/Dc of the silicon oxide-coated iron oxide particles was from 113.4% to 131.0%. From the XRD measurement results of the silicon oxide-coated iron oxide particles in Example 6, peaks derived from iron oxide ($Fe_2O_3$) were observed, and no other peaks were observed.

Example 7

The oxide raw material liquid for core, the oxide precipitation solvent, and the oxide raw material liquid for shell were prepared using the high-speed rotary dispersion emulsification apparatus CLEAMIX (product name: CLM-2.2 S, M. Technique Co., Ltd.). Specifically, based on the formulation of the oxide raw material liquid for core shown in Example 7 of Table 9, the components of the oxide raw material liquid for core were mixed homogeneously by stirring using CLEARMIX at preparation temperature of 40° C. and at the rotor rotational speed of 20000 rpm for 30 min to prepare the oxide raw material liquid for core. Based on the formulation of the oxide precipitation solvent shown in Example 7 of Table 9, the components of the oxide precipitation solvent were mixed homogeneously by stirring using CLEARMIX at preparation temperature of 45° C. and at the rotor rotational speed of 15000 rpm for 30 min to prepare the oxide precipitation solvent. Furthermore, based on the formulation of the oxide raw material liquid for shell shown in Example 7 of Table 9, the components of the silicon oxide raw material liquid were mixed homogeneously by stirring using CLEARMIX at preparation temperature of 20° C. and at the rotor rotational speed of 6000 rpm for 10 min to prepare the oxide raw material liquid for shell.

Regarding the substances represented by the chemical formula and abbreviations set forth in Table 9, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.).

TABLE 9

| Example 7 | | | | | | | | |
|---|---|---|---|---|---|---|---|---|
| Formulation of First fluid (Liquid A) (Oxide raw material liquid for core) | | | | | Formulation of Second fluid (Liquid B) (Oxide precipitation solvent) | | | |
| Formulation [wt %] | | | | | Formulation [wt %] | | | |
| Raw material | [wt %] | Raw material | [wt %] | pH / pH [° C.] | Raw material | [wt %] | Raw material | [wt %] | pH / pH [° C.] |
| $Fe(NO_3)_3$ $9H_2O$ | 2.00 | Pure water | 98.00 | 1.8 / 26.6 | NaOH | 9.00 | Pure water | 91.00 | >14 / — |

| Formulation of Third fluid (Liquid C) | | | | | | | |
|---|---|---|---|---|---|---|---|
| Formulation [wt %] | | | | | | | |
| Raw material | [wt %] | Raw material | [wt %] | Raw material | [wt %] | pH | pH [° C.] |
| Pure water | 93.64 | 97 wt % $H_2SO_4$ | 3.86 | TEOS | 2.50 | <1 | — |

TABLE 10

| Example 7 | | | | | | | | | | |
|---|---|---|---|---|---|---|---|---|---|---|
| Introduction flow rate [ml/min] | | | Introduction temperature (liquid sending temperature) [° C.] | | | Introduction pressure (liquid sending pressure) [MPaG] | | | Discharged liquid | |
| Liquid A | Liquid B | Liquid C | Liquid A | Liquid B | Liquid C | Liquid A | Liquid B | Liquid C | pH | Temperature [° C.] |
| 900 | 100 | 150 | 140 | 80 | 60 | 0.432 | 0.55 | 0.55 | 12.29 | 34.6 |

| Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|
| | Calcurated value | EDS | | | |
| — | 0.81 | 0.84 | 15.46 | 9.49 | 162.9% |

Figure 14:
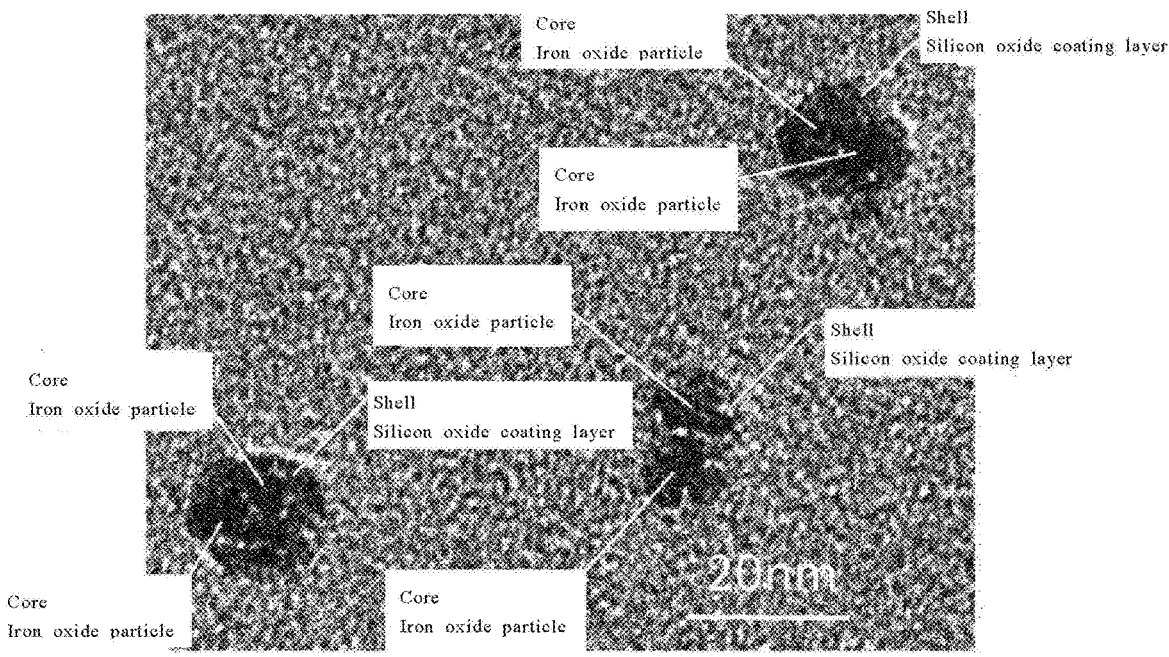
FIG. 14 shows a TEM photograph of the silicon oxide-coated iron oxide particles obtained in Example 7 of the present invention.

Then, the prepared oxide raw material liquid for core, the oxide precipitation solvent, and the oxide raw material liquid for shell were mixed in the same fluid processing apparatus as in Example 4. Table 10 shows the operating conditions of the fluid processing apparatus. The core conversion particle diameter (Dc) described in Table 10 is the maximum distance between two points on the outer periphery of the core aggregate formed by the iron oxide particles, and the average value of the measured diameters of 100 aggregates is shown. The methods of washing, analysis and evaluation of particles are the same as in Example 1. A TEM photograph of the silicon oxide-coated iron oxide particles obtained in Example 7 is shown in FIG. 14. The core is an aggregate of a plurality of primary iron oxide particles, and the silicon oxide-coated iron oxide particles wherein the aggregate is coated with silicon oxide, was observed. The coating layer (shell) of the silicon oxide on the surface of the aggregate of iron oxide particles was observed. Regarding the state of the coating, it was also observed that the aggregates were mainly uniformly coated, but a part of the aggregates were not coated. Further, the particle diameter of the silicon oxide-coated iron oxide particles obtained in Example 7 was 50 nm or less. Not shown details of the particle diameter D or the core particle diameter Dc in FIG. 14, but D/Dc was about 162.9%. In the XRD measurement results, peaks of α-$Fe_2O_3$ (hematite) were detected as in Example 4, and the FT-IR measurement results were similar to those in Example 4.

In the XRD measurement results, peaks of α-$Fe_2O_3$ (hematite) were clearly detected in all conditions in Examples 4 to 7 and Comparative Example 5. As described above, in Examples, peaks of silicon oxide coating on the surface of the particles were not detected, and thus, the silicon oxide is considered to be amorphous.

Comparative Example 6

The oxide raw material liquid for core, the oxide precipitation solvent, and the oxide raw material liquid for shell were prepared using the high-speed rotary dispersion emulsification apparatus CLEAMIX (product name: CLM-2.2 S, M. Technique Co., Ltd.). Specifically, based on the formulation of the oxide raw material liquid for core shown in Comparative Example 6 of Table 11, the components of the oxide raw material liquid for core were mixed homogeneously by stirring using CLEARMIX at preparation temperature of 40° C. and at the rotor rotational speed of 20000 rpm for 30 min to prepare the oxide raw material liquid for core. Based on the formulation of the oxide precipitation solvent shown in Comparative Example 6 of Table 11, the components of the oxide precipitation solvent were mixed homogeneously by stirring using CLEARMIX at preparation temperature of 45° C. and at the rotor rotational speed of 15000 rpm for 30 min to prepare the oxide precipitation solvent. Furthermore, based on the formulation of the oxide raw material liquid for shell shown in Comparative Example 6 of Table 11, the components of the silicon oxide raw material liquid were mixed homogeneously by stirring using CLEARMIX at preparation temperature of 20° C. and at the rotor rotational speed of 6000 rpm for 10 min to prepare the oxide raw material liquid for shell.

Figure 12:
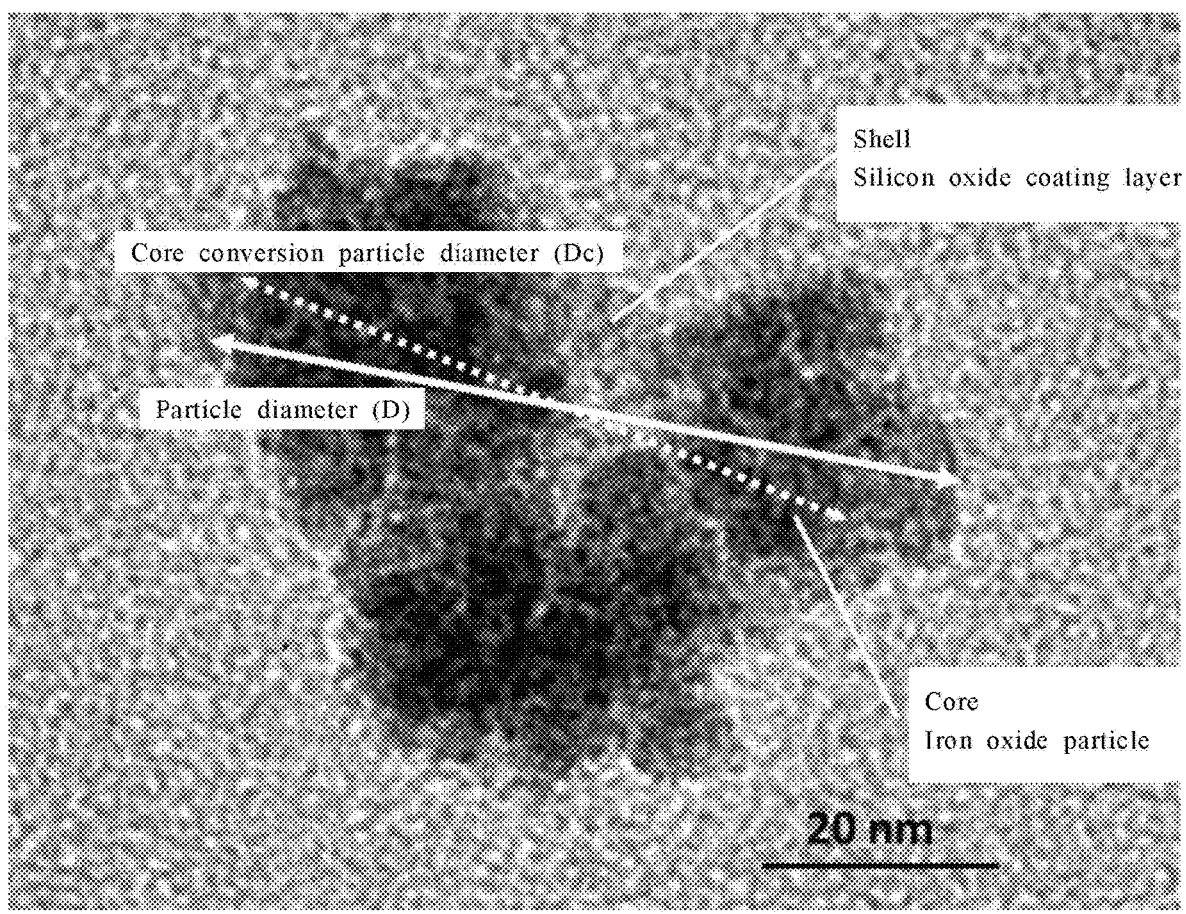
FIG. 12 shows a TEM photograph of the silicon oxide-coated iron oxide particles obtained in Comparative Example 6 of the present invention.

Regarding the substances represented by the chemical formula and abbreviations set forth in Table 11, 60 wt % $HNO_3$ is concentrated nitric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3$ $9H_2O$ is iron nitrate nonahydrate (Kanto Chemical Co., Inc.). The methods of washing, analysis and evaluation of particles are the same as in Example 1.

apparatus as in Example 4. Table 12 shows the operating conditions of the fluid processing apparatus. The methods of washing, analysis and evaluation of particles are the same as in Example 1. By the TEM photograph of the silicon oxide-coated oxide particles obtained in Comparative Example 6, iron oxide particles in which the entire surface of one iron oxide particle was coated uniformly with silicon oxide were not observed, but many particles in which the surface of an aggregate of a plurality of iron oxide particles was coated with silicon oxide were observed. A TEM photograph of the silicon oxide-coated oxide particles obtained in Comparative Example 6 is shown in FIG. 12. As shown in FIG. 12, it was observed that the surface of a core aggregate of primary iron oxide particles was coated with shell silicon oxide. There was a part in which a core primary particle of iron oxide is unclear. Further, the particle diameter of the silicon oxide-coated iron oxide particles obtained in Comparative Example 6 exceeded 50 nm. In the XRD measurement results, peaks of $\alpha$-$Fe_2O_3$ (hematite) were detected as in Example 4, and the FT-IR measurement results were similar to those in Example 4.

FIG. 10 shows the reflection spectra for a wavelength of 250 to 800 nm of the silicon oxide-coated iron oxide particle powders obtained in Example 4 and Example 7, and of the iron oxide particle powders which surface is not coated with silicon oxide obtained in Comparative Example 5, and of the

TABLE 11

| Comparative Example 6 | | | | | | | | | |
|---|---|---|---|---|---|---|---|---|---|
| Formulation of First fluid (Liquid A) (Oxide raw material liquid for core) | | | | | Formulation of Second fluid (Liquid B) (Oxide precipitation solvent) | | | | |
| Formulation [wt %] | | | | | Formulation [wt %] | | | | |
| Raw material | [wt %] | Raw material | [wt %] | pH | pH [° C.] | Raw material | [wt %] | Raw material | [wt %] | pH | pH [° C.] |
| $Fe(NO_3)_3$ $9H_2O$ | 2.00 | Pure water | 98.00 | 1.8 | 26.6 | NaOH | 9.00 | Pure water | 91.00 | >14 | — |
| Formulation of Third fluid (Liquid C) | | | | | | | | | |
| Formulation [wt %] | | | | | | | | | |
| Raw material | [wt %] | Raw material | [wt %] | Raw material | [wt %] | pH | pH [° C.] |
| Pure water | 97.52 | 60 wt % $H_2SO_4$ | 2.11 | TEOS | 0.37 | <1 | — |

TABLE 12

| Comparative Example 6 | | | | | | | | | | |
|---|---|---|---|---|---|---|---|---|---|---|
| Introduction flow rate [ml/min] | | | Introduction temperature (liquid sending temperature) [° C.] | | | Introduction pressure (liquid sending pressure) [MPaG] | | | Discharged liquid | |
| Liquid A | Liquid B | Liquid C | Liquid A | Liquid B | Liquid C | Liquid A | Liquid B | Liquid C | pH | Temperature [° C.] |
| 400 | 50 | 50 | 143 | 83 | 25 | 0.329 | 0.50 | 0.50 | 12.99 | 23.4 |

Then, the prepared oxide raw material liquid for core, the oxide precipitation solvent, and the oxide raw material liquid for shell were mixed in the same fluid processing silicon oxide-coated iron oxide particle powders provided with acetyl groups obtained in Example 5, and of the silicon oxide-coated iron oxide particle powders wherein an aggregate of a plurality of iron oxide particles is coated with silicon oxide obtained in Comparative Example 6 respectively. Incidentally, transmission spectrum of a dispersion liquid prepared by dispersing the silicon oxide-coated iron oxide obtained in Example 4 and the iron oxide obtained in Comparative Example 5 in propylene glycol at an iron oxide concentration of 0.05 wt % was measured. As a result, substantially the same results were obtained in the transmission spectrum of the dispersion of Example 4 and the transmission spectrum of the dispersion of Comparative Example 5 as shown in FIG. 15. Further, transmission spectrum of a dispersion liquid prepared by dispersing the silicon oxide-coated iron oxide obtained in Example 5 in butyl acetate at an iron oxide concentration of 0.05 wt % was measured. As a result, the measured transmission spectrum was substantially the same as the above transmission spectrum of each dispersion of Example 4 and Comparative Example 5.

As shown in FIG. 10, the reflectivity of the silicon oxide-coated iron oxide particles obtained in Example 4 for the light of the wavelength of around 550 to 800 nm, was low as compared with that of the iron oxide particles obtained in Comparative Example 5. This shows the result that amorphous silicon oxide coating gives a change in color characteristics. Further, the reflectivity of the silicon oxide-coated iron oxide particles obtained in Example 5 for the light of the wavelength of around 550 to 800 nm, increased as compared with that of the silicon oxide-coated iron oxide particles obtained in Example 4. This shows that the color characteristics change by addition of an acetyl group to the silicon oxide-coated iron oxide particles. This result indicates that the color characteristics change by changing a functional group contained in the particles. Also, the reflectivity of the silicon oxide-coated iron oxide particles obtained in Example 6 for the light of the wavelength of around 550 to 800 nm, decreased as compared with that of the silicon oxide-coated iron oxide particles obtained in Example 5, and was higher than that of the silicon oxide-coated iron oxide particles obtained in Example 4 (not shown in FIG). However, significant difference in reflectivity was not observed between the iron oxide particles of Comparative Example 5 without silicon oxide coating on their surface and the iron oxide aggregate coated with silicon oxide of Comparative Example 6 (the silicon oxide-coated iron oxide which particle diameter exceeds 50 nm). Further, the reflectivity for the light of the wavelength of 550 to 800 nm of the silicon oxide-coated iron oxide particles obtained in Example 7 wherein an aggregate of a plurality of iron oxide particles was coated with silicon oxide (the silicon oxide-coated iron oxide which particle diameter is 50 nm or less), was slightly higher than that of Example 4, and was lower than that of the silicon oxide-coated iron oxide particles exceeding 50 nm as in Comparative Example 6. It was found that reflectivity could be controlled by a coating condition of the surface of iron oxide particles with silicon oxide. On the other hand, it was found that the effect on color characteristics was lowered when an aggregate of iron oxide particles, particularly an aggregate of iron oxide particles having more than 50 nm diameter were coated with silicon oxide.

From the above, in the silicon oxide-coated oxide particles of the present invention, the amorphous silicon oxide covering at least a part of the surface of the oxide particles can be used for the purpose of controlling color characteristics, in particular reflectivity. For example, it was shown that the silicon oxide-coated zinc oxide particles obtained in Example 1 have higher reflectivity for the light of the wavelength of around 380 to 780 nm in the visible region, and reflect a white light effectively as compared with that of the iron oxide particles obtained in Comparative Example 1. When reflectivity for around 550 to 800 nm is reduced as compared with that of the iron oxide particles obtained in Comparative Example 5, like the silicon oxide-coated iron oxide particles obtained in Example 4, the particles can be used as a deep red color. When reflectivity for around 550 to 800 nm is higher as compared with that of Example 4, like the silicon oxide-coated iron oxide particles obtained in Example 5, the particles can be used as a lighter red color. Thus, it is possible to use properly silicon oxide-coated oxide particles depending on a desired color and designability.

The invention claimed is:

1. A composition for coating, which is used by blending the composition for coating to a paint constituting a coated body in which weather resistance is required,
   wherein the composition for coating comprises silicon oxide-coated oxide particles wherein at least a part of the surface of the oxide particles is coated with the silicon oxide,
   wherein the silicon oxide is amorphous,
   wherein the silicon oxide-coated oxide particles comprise an acetyl group as a functional group, and
   wherein the silicon oxide-coated oxide particles are constituted so that reflectivity for the light of 550 to 800 nm is lower than that of oxide particles which surface is not coated with silicon oxide.

2. A composition for coating, which is used by blending the composition for coating to a paint constituting a coated body in which weather resistance is required,
   wherein the composition for coating comprises silicon oxide-coated oxide particles wherein at least a part of the surface of the oxide particles is coated with the silicon oxide,
   wherein the oxide particles are zinc oxide particles,
   wherein the silicon oxide-coated oxide particles are those wherein at least a part of the surface of one oxide particle or at least a part of the surface of an aggregate of a plurality of oxide particles is coated with silicon oxide,
   wherein a particle diameter of the one oxide particle or a diameter of the aggregate is 100 nm or less, and the primary particle diameter of the silicon oxide-coated oxide particles is 100.5% or more and 190% or less relative to the primary particle diameter of the one oxide particle or the diameter of the aggregate, and
   wherein the silicon oxide-coated oxide particles are constituted so that reflectivity for the light of 380 to 780 nm is higher than that of oxide particles which surface is not coated with silicon oxide.

3. The silicon oxide-coated oxide composition for coating according to claim 2, wherein the silicon oxide comprises amorphous silicon oxide.

4. The silicon oxide-coated oxide composition for coating according to claim 2, wherein the silicon oxide-coated oxide particles comprise an acetyl group as a functional group.

5. A composition for coating, which is used by blending the composition for coating to a paint constituting a coated body in which weather resistance is required,
   wherein the composition for coating comprises silicon oxide-coated oxide particles wherein at least a part of the surface of the oxide particles is coated with the silicon oxide,
   wherein the oxide particles are hematite particles, wherein the silicon oxide-coated oxide particles are those wherein at least a part of the surface of one oxide particle or at least a part of the surface of an aggregate of a plurality of oxide particles is coated with silicon oxide, wherein a particle diameter of the one oxide particle or a diameter of the aggregate is 50 nm or less, and the primary particle diameter of the silicon oxide-coated oxide particles is 100.5% or more and 190% or less relative to the primary particle diameter of the one oxide particle or the diameter of the aggregate, and wherein the silicon oxide-coated oxide particles are constituted so that reflectivity for the light of 550 to 800 nm is lower than that of oxide particles which surface is not coated with silicon oxide.

6. The silicon oxide-coated oxide composition for coating according to claim 5, wherein the silicon oxide-coated oxide particles comprise an acetyl group as a functional group.

7. The silicon oxide-coated oxide composition for coating according to claim 5, wherein the silicon oxide comprises amorphous silicon oxide.

8. A method of producing the composition for coating according to claim 1 comprising oxide particles, which is used by blending the composition for coating to a paint constituting a coated body in which weather resistance is required, wherein color characteristics of the oxide particles are controlled by producing the oxide particles by selecting presence or absence of amorphous silicon oxide covering at least a part of the surface of the oxide particles, and presence or absence of an acetyl group as a functional group contained in the silicon oxide-coated oxide particles.

* * * * *